US008637481B2

(12) United States Patent
Liu et al.

(10) Patent No.: US 8,637,481 B2
(45) Date of Patent: Jan. 28, 2014

(54) SENSITIZING AGENTS FOR CANCER THERAPY, METHODS OF USE AND METHODS FOR THE IDENTIFICATION THEREOF

(75) Inventors: Fei-Fei Liu, Toronto (CA); Emma Ito, Toronto (CA); Inki Kim, Pyongtaek (KR)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 13/264,598

(22) PCT Filed: Apr. 12, 2010

(86) PCT No.: PCT/CA2010/000569
§ 371 (c)(1),
(2), (4) Date: Dec. 2, 2011

(87) PCT Pub. No.: WO2010/118524
PCT Pub. Date: Oct. 21, 2010

(65) Prior Publication Data
US 2012/0094900 A1     Apr. 19, 2012

Related U.S. Application Data

(60) Provisional application No. 61/170,145, filed on Apr. 17, 2009, provisional application No. 61/170,148, filed on Apr. 17, 2009.

(51) Int. Cl.
C12N 15/11    (2006.01)
C12Q 1/68     (2006.01)
C07H 21/04    (2006.01)

(52) U.S. Cl.
USPC .......................... 514/44 A; 435/6.1; 536/24.5

(58) Field of Classification Search
None
See application file for complete search history.

(56) References Cited

U.S. PATENT DOCUMENTS

2006/0094781 A1    5/2006  Eckhouse et al. ............. 514/551
2010/0331210 A1*   12/2010 Gabrin et al. .................. 506/10

FOREIGN PATENT DOCUMENTS

WO    WO 2008021183 A2 *  2/2008

OTHER PUBLICATIONS

Whysner et al., Hepatocellular iron accumulation and increaed cell proliferation in polychlorinated biphenyl-exposed sprague-dawley rats and the development of hepatocarcinogenesis, 2001, Toxicological Sciences, vol. 62, pp. 36-45.*

Wang et al., Cancer cell killing via ROS, to increase or decrease, that is the question, 2008, Cancer Biology & Therapy, vol. 7, pp. 1875-1884.*

Alexandre J, Batteux F, Nicco C, et al., "Accumulation of hydrogen peroxide is an early and crucial step for paclitaxel-induced cancer cell death both in vitro and in vivo", *Int. J. Cancer* 2006; 119: 41-8.

Berg K, Selbo PK, Weyergang A, et al., "Porphyrin-related photosensitizers for cancer imaging and therapeutic applications", *J Microsc.* 2005; 218: 133-147.

Bonner JA, Harari PM, Giralt J, et al., "Radiotherapy plus cetuximab for locoregionally advanced head and neck cancer: 5-year survival data from a phase 3 randomised trial, and relation between cetuximab-induced rash and survival", *Lancet Oncol.* 2010; 11:21-28.

Bourhis J, Overgaard J, Audry H, et al. "Hyperfractionated or accelerated radiotherapy in head and neck cancer: a meta-analysis", *Lancet* 2006; 368: 843-854.

Brown, S. B. el al., "The present and future role of photodynamic therapy in cancer treatment", *The Lancet Oncology* 5:497-508, 2004.

Chia MC, Shi W, Li JH, et al., "A conditionally replicating adenovirus for nasopharyngeal carcinoma gene therapy", *Mol. Ther.* 2004; 9: 804-817.

Cummings B, Keane T, Pintilie M, et al., "Five year results of a randomized trial comparing hyperfractionated to conventional radiotherapy over four weeks in locally advanced head and neck cancer", *Radiother. Oncol.* 2007; 85:7-16.

Extended European Search Report issued in European Patent Application No. 10764022.9, dated Mar. 12, 2012.

Hwang PM, Bunz F, Yu J, et al., "Ferredoxin reductase affects p53-dependent, 5-flourouracil-induced apoptosis in colorectal cancer cells", *Nat. Med* 2001; 7: 1111-7.

Ito E, Yue S, Moriyama EH, et al., "Uroporphyrinogen decarboxylase is a radiosensitizing target for head and neck cancer", *Sci. Transl. Med.* 2011; 3: 67ra7.

Katz, D. et al., "On the Path to Seeking Novel Radiosensitizers", *Int. J. Radiation Oncology Biol. Phys.* 73(4):988-996, 2009.

Kennedy JC, Pottier RH, "Endogenous protoporphyrin IX, a clinically useful photosensitizer for photodynamic therapy", *J. Photochem. Photobiol. B.* 1992; 14: 275-292.

Kennedy JC, Pottier RH, Pross DC, "Photodynamic therapy with endogenous protoporphyrin IX: basic principles and present clinical experience", *J. Photochem. Photobiol. B.* 1990; 6: 143-148.

Lambrecht RW, Thapar M, Bonkovsky HL, "Genetic aspects of porphyria cutanea tarda", *Semin. Liver Dis.* 2007; 27: 99-108.

Li JH, Shi W, Chia M, et al., "Efficacy of targeted FasL in nasopharyngeal carcinoma", *Mol. Ther.* 2003; 8: 964-973.

Navone NM, Frisardi AL, Resnik ER, Batlle AM, Polo CF, "Porphyrin biosynthesis in human breast cancer. Preliminary mimetic in vitro studies", *Med. Sci. Res.* 1988; 16: 61-62.

Navone NM, Polo CF, Frisardi AL, Andrade NE, Battle AM, "Heme biosynthesis in human breast cancer—mimetic "in vitro" studies and some heme enzymic activity levels", *Int. J. Biochem.* 1990; 22:1407-1411.

Pelicano H, Carney D, Huang P, "ROS stress in cancer cells and therapeutic implications", *Drug Resist. Updat.* 2004; 7: 97-110.

(Continued)

*Primary Examiner* — Dana Shin
(74) *Attorney, Agent, or Firm* — Fulbright & Jaworski LLP

(57) ABSTRACT

There is provided herein methods, compounds and methods for identifying compounds, for sensitizing a subject with cancer to a cancer therapy by inhibiting or down-regulating UROD.

9 Claims, 7 Drawing Sheets

(56) References Cited

OTHER PUBLICATIONS

Pignon JP, le Maitre A, Maillard E, Bourhis J., "Meta-analysis of chemotherapy in head and neck cancer (MACH-NC); an update on 93 randomised trials and 17,346 patients", *Radiother. Oncol.* 2009; 92: 4-14.

Yip KW, Ito E, Mao X, et al., "Potential use of alexidine dihydrochloride as an apoptosis-promoting anticancer agent", *Mol. Cancer Ther.* 2006; 5: 2234-2240.

Yip KW, Li A, Li JH, et al., "Potential utility of BimS as a novel apoptotic therapeutic molecule", *Mol. Ther.* 2004; 10: 533-544.

Yip KW, Mao X, Au PY, et al., "Benzethonium chloride: a novel anticancer agent identified by using a cell-based small-molecule screen", *Clin. Cancer Res.* 2006; 12: 5557-5569.

Yip KW, Mocanu JD, Au PY, et al., "Combination bcl-2 antisense and radiation therapy for nasopharyngeal cancer", *Clin. Cancer Res.* 2005; 11: 8131-8144.

* cited by examiner

SEQUENCE LISTING

```
<160> NUMBER OF SEQ ID NOS: 20

<210> SEQ ID NO 1
<211> LENGTH: 21
<212> TYPE: DNA
<213> ORGANISM: Artificial Sequence
<220> FEATURE:
<223> OTHER INFORMATION: Synthetic primer

<400> SEQUENCE: 1
gacggtgaca ttgcagggca a                                        21

<210> SEQ ID NO 2
<211> LENGTH: 21
<212> TYPE: DNA
<213> ORGANISM: Artificial Sequence
<220> FEATURE:
<223> OTHER INFORMATION: siRNA strand

<400> SEQUENCE: 2
cggugacauu gcagggcaat t                                        21

<210> SEQ ID NO 3
<211> LENGTH: 21
<212> TYPE: DNA
<213> ORGANISM: Artificial Sequence
<220> FEATURE:
<223> OTHER INFORMATION: siRNA strand

<400> SEQUENCE: 3
uugcccugca augucaccgt c                                        21

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
ctcaagtacc actaacacag a                                        21

<210> SEQ ID NO 5
<211> LENGTH: 21
<212> TYPE: DNA
<213> ORGANISM: Artificial Sequence
<220> FEATURE:
<223> OTHER INFORMATION: siRNA strand

<400> SEQUENCE: 5
caaguaccac uaacacagat t                                        21

<210> SEQ ID NO 6
<211> LENGTH: 21
<212> TYPE: RNA
<213> ORGANISM: Artificial Sequence
<220> FEATURE:
```

<223> OTHER INFORMATION: siRNA strand

<400> SEQUENCE: 6
ucuguguuag ugguacuuga g                                         21

<210> SEQ ID NO 7
<211> LENGTH: 6321
<212> TYPE: DNA
<213> ORGANISM: Artificial Sequence
<220> FEATURE:
<223> OTHER INFORMATION: Synthetic primer

<400> SEQUENCE: 7

| | | | | |
|---|---|---|---|---|
| tcctgcatct | tttaatcaaa | tcccaagatg | tgtataaacg | cgccggtatg | tacaggaaga | 60 |
| ggtttatact | aaactgttac | attgcaaacg | tggtttcgtg | tgccaagtgt | gaaaaccgat | 120 |
| gtttaatcaa | ggctctgacg | catttctaca | accacgactc | caagtgtgtg | ggtgaagtca | 180 |
| tgcatctttt | aatcaaatcc | caagatgtgt | ataaaccacc | aaactgccaa | aaatgaaaaa | 240 |
| ctgtcgacaa | gctctgtccg | tttgctggca | actgcaaggg | tctcaatcct | atttgtaatt | 300 |
| attgaataat | aaaacaatta | taatgtcaa | atttgttttt | tattaacgat | acaaaccaaa | 360 |
| cgcaacaaga | acatttgtag | tattatctat | aattgaaaac | gcgtagttat | aatcgctgag | 420 |
| gtaatattta | aaatcatttt | caaatgattc | acagttaatt | tgcgacaata | taattttatt | 480 |
| ttcacataaa | ctagacgcct | tgtcgtcttc | ttcttcgtat | tccttctctt | tttcatttt | 540 |
| ctcttcataa | aaattaacat | agttattatc | gtatccatat | atgtatctat | cgtatagagt | 600 |
| aaatttttttg | ttgtcataaa | tatatatgtc | ttttttaatg | gggtgtatag | taccgctgcg | 660 |
| catagttttt | ctgtaattta | caacagtgct | attttctggt | agttcttcgg | agtgtgttgc | 720 |
| tttaattatt | aaatttatat | aatcaatgaa | tttgggatcg | tcggttttgt | acaatatgtt | 780 |
| gccggcatag | tacgcagctt | cttctagttc | aattacacca | ttttttagca | gcaccggatt | 840 |
| aacataactt | tccaaaatgt | tgtacgaacc | gttaaacaaa | aacagttcac | ctccctttc | 900 |
| tatactattg | tctgcgagca | gttgtttgtt | gttaaaaata | acagccattg | taatgagacg | 960 |
| cacaaactaa | tatcacaaac | tggaaatgtc | tatcaatata | tagttgctga | tggccggccg | 1020 |
| taatgagacg | cacaaactaa | tatcacaaac | tggaaatgtc | tatcaatata | tagttgctct | 1080 |
| agttattaat | agtaatcaat | tacggggtca | ttagttcata | gcccatatat | ggagttccgc | 1140 |
| gttacataac | ttacggtaaa | tggcccgcct | ggctgaccgc | ccaacgaccc | ccgcccattg | 1200 |
| acgtcaataa | tgacgtatgt | tcccatagta | acgccaatag | ggactttcca | ttgacgtcaa | 1260 |
| tgggtggagt | atttacggta | aactgcccac | ttggcagtac | atcaagtgta | tcatatgcca | 1320 |
| agtacgcccc | ctattgacgt | caatgacggt | aaatggcccg | cctggcatta | tgcccagtac | 1380 |
| atgaccttat | gggactttcc | tacttggcag | tacatctacg | tattagtcat | cgctattacc | 1440 |
| atgcatggtc | gaggtgagcc | ccacgttctg | cttcactctc | cccatctccc | ccccctcccc | 1500 |
| acccccaatt | ttgtatttat | ttatttttta | attattttgt | gcagcgatgg | gggcgggggg | 1560 |
| ggggggggggg | cgcgcgccag | gcgggcgggg | cggggcgag | gggcggggcg | gggcgaggcg | 1620 |
| gagaggtgcg | gcggcagcca | atcagagcgg | cgcgctccga | aagtttcctt | ttatggcgag | 1680 |
| gcggcggcgg | cggcggccct | ataaaaagcg | aagcgcgcgg | cgggcgggag | tcgctgcgcg | 1740 |
| ctgccttcgc | cccgtgcccc | gctccgccgc | cgcctcgcgc | cgcccgcccc | ggctctgact | 1800 |
| gaccgcgtta | ctcccacagg | tgagcgggcg | ggacggccct | tctccttcgg | gctgtaatta | 1860 |
| gcgcttggtt | taatgacggc | ttgtttcttt | tctgtggctg | cgtgaaagcc | ttgagggget | 1920 |

```
ccgggagggc cctttgtgcg gggggagcgg ctcgggctg tccgcgggg gacggctgcc   1980
ttcgggggg acgggcagg gcggggttcg gcttctggcg tgtgaccggc ggctctagag    2040
cctctgctaa ccatgttcat gccttcttct ttttcctaca gctcctgggc aacgtgctgg  2100
ttattgtgct gtctcatcat tttggcaaag aattggatcg gaccgaaatt aatacgactc  2160
actatagggg aattgtgagc ggataacaat tccccggagt taatccggga cctttaattc  2220
aacccaacac aatatattat agttaaataa gaattattat caaatcattt gtatattaat  2280
taaaatacta tactgtaaat tacattttat ttacaatcaa aggagatata ccatggaagc  2340
caacggcctc ggccctcagg gcttccccga gctgaagaac gacaccttcc tgagagccgc  2400
ctggggcgag gaaaccgact acaccccgt gtggtgcatg agacaggccg gcagatatct  2460
ccccgagttc cggagacaa gagccgccca ggacttcttc agcacctgtc ggagccccga   2520
ggcctgttgc gagctgactc tgcagcctct gagaagattc cccctggacg ccgccatcat  2580
cttcagcgac atcctggtgg tgcctcaggc cctgggcatg gaagtgacaa tggtgcccgg  2640
caagggccct agcttccctg agcccctgcg ggaggaacag gacctggaac ggctgagaga  2700
tcccgaggtg gtggccagcg agctgggcta cgtgttccag gccatcaccc tgaccagaca  2760
gaggctggca ggcagagtgc ctctgatcgg cttcgctggc gccccttgga ccctgatgac  2820
ctacatggtg gagggcggag gcagctctac aatgggccag gccaagcggt ggctctatca  2880
gaggccccag gccagccacc agctgctgag aatcctgacc gacgccctgg tgccttacct  2940
ggtcggccag gtcgtggctg gcgctcaggc tctgcagctg ttcgagagcc acgccggaca  3000
tctgggcccc cagctgttca caagttcgc cctgccctac atcagggacg tggccaaaca   3060
ggtcaaggcc agactgagag aggccggact ggccccgtg cccatgatca tcttcgccaa   3120
ggacggccac ttcgccctgg aagaactggc tcaggctggc tacgaagtgg tcggcctgga  3180
ttggaccgtg gccccaaga aagcccggga gtgcgtgggc aagaccgtga cactgcaggg   3240
caacctggac ccttgtgccc tgtacgccag cgaggaagag atcggccagc tggtcaagca  3300
gatgctggac gacttcggcc cccaccggta cattgccaac ctgggccacg gcctgtaccc  3360
cgacatggac cctgagcacg tgggcgcctt cgtggatgcc gtgcacaagc actctcggct  3420
gctgcggcag aaccaccacc accatcacca tcatcaccac cactagtgac tcgagaagcg  3480
ttgaaatagc gtacaagtcg agcaccacca tcaccatcac catcactaag tgattaacct  3540
caggtgcagg ctgcctatca gaaggtggtg gctggtgtgg ccaatgccct ggctcacaaa  3600
taccactgag atcgatcttt ttccctctgc caaaaattat ggggacatca tgaagccct   3660
tgagcatctg acttctggct aataaaggaa atttattttc attgcaatag tgtgttggaa  3720
ttttttgtgt ctctcactcg gaaggacata tgggagggca aatcatttaa acatcagaa   3780
tgagtatttg gtttagagtt tggcaacata tgcccatatg taactagcat aaccccttgg  3840
ggcctctaaa cgggtcttga ggggttttt gctgaaagca tgcggaggaa attctccttg   3900
aagtttccct ggtgttcaaa gtaaaggagt ttgcaccaga cgcacctctg ttcactggtc  3960
cggcgtatta aaacacgata cattgttatt agtacattta ttaagcgcta gattctgtgc  4020
gttgttgatt tacagacaat tgttgtacgt attttaataa ttcattaaat ttataatctt  4080
tagggtggta tgttagagcg aaaatcaaat gattttcagc gtctttatat ctgaatttaa  4140
atattaaatc ctcaatagat tgtaaaata ggtttcgatt agtttcaaac aagggttgtt   4200
tttccgaacc gatggctgga ctatctaatg gattttcgct caacgccaca aaacttgcca  4260
aatcttgtag cagcaatcta gctttgtcga tattcgtttg tgttttgttt tgtaataaag  4320
```

```
gttcgacgtc gttcaaaata ttatgcgctt ttgtatttct ttcatcactg tcgttagtgt    4380
acaattgact cgacgtaaac acgttaaata gagcttggac atatttaaca tcgggcgtgt    4440
tagctttatt aggccgatta tcgtcgtcgt cccaaccctc gtcgttagaa gttgcttccg    4500
aagacgattt tgccatagcc acacgacgcc tattaattgt gtcggctaac acgtccgcga    4560
tcaaatttgt agttgagctt tttggaattg cgatcgcata acttcgtata gcatacatta    4620
tacgaagtta taagctcgga acgctgcgct cggtcgttcg gctgcggcga gcggtatcag    4680
ctcactcaaa ggcggtaata cggttatcca cagaatcagg ggataacgca ggaaagaaca    4740
tgtgagcaaa aggccagcaa aaggccagga accgtaaaaa ggccgcgttg ctggcgtttt    4800
tccataggct ccgcccccctg acgagcatca caaaaatcga cgctcaagtc agaggtggcg    4860
aaacccgaca ggactataaa gataccaggc gtttccccct ggaagctccc tcgtgcgctc    4920
tcctgttccg accctgccgc ttaccggata cctgtccgcc tttctccctt cgggaagcgt    4980
ggcgctttct catagctcac gctgtaggta tctcagttcg gtgtaggtcg ttcgctccaa    5040
gctgggctgt gtgcacgaac cccccgttca gcccgaccgc tgcgccttat ccggtaacta    5100
tcgtcttgag tccaacccgg taagacacga cttatcgcca ctggcagcag ccactggtaa    5160
caggattagc agagcgaggt atgtaggcgg tgctacagag ttcttgaagt ggtggcctaa    5220
ctacggctac actagaagaa cagtatttgg tatctgcgct ctgctgaagc cagttacctt    5280
cggaaaaaga gttggtagct cttgatccgg caaacaaacc accgctggta gcggtggttt    5340
ttttgtttgc aagcagcaga ttacgcgcag aaaaaaagga tctcaagaag atcctttgtt    5400
accaatgctt aatcagtgag gcacctatct cagcgatctg tctatttcgt tcatccatag    5460
ttgcctgact ccccgtcgtg tagataacta cgatacggga gggcttacca tctggcccca    5520
gtgctgcaat gataccgcga gacccacgct caccggctcc agatttatca gcaataaacc    5580
agccagccgg aagggccgag cgcagaagtg gtcctgcaac tttatccgcc tccatccagt    5640
ctattaattg ttgccgggaa gctagagtaa gtagttcgcc agttaatagt ttgcgcaacg    5700
ttgttgccat tgctacaggc atcgtggtgt cacgctcgtc gtttggtatg gcttcattca    5760
gctccggttc ccaacgatca aggcgagtta catgatcccc catgttgtgc aaaaaagcgg    5820
ttagctcctt cggtcctccg atcgttgtca gaagtaagtt ggccgcagtg ttatcactca    5880
tggttatggc agcactgcat aattctctta ctgtcatgcc atccgtaaga tgcttttctg    5940
tgactggtga gtactcaacc aagtcattct gagaatagtg tatgcggcga ccgagttgct    6000
cttgcccggc gtcaatacgg gataataccg cgccacatag cagaacttta aaagtgctca    6060
tcattggaaa acgttcttcg ggcgaaaac  tctcaaggat cttaccgctg ttgagatcca    6120
gttcgatgta acccactcgt gcacccaact gatcttcagc atcttttact ttcaccagcg    6180
tttctgggtg agcaaaaaca ggaaggcaaa atgccgcaaa aaagggaata agggcgacac    6240
ggaaatgttg aatactcata ctcttccttt tcaatatta ttgaagcatt tatcagggtt    6300
attgtctcat gtccgcgcgt t                                              6321
```

<210> SEQ ID NO 8
<211> LENGTH: 5766
<212> TYPE: DNA
<213> ORGANISM: Artificial Sequence
<220> FEATURE:
<223> OTHER INFORMATION: Synthetic primer

<400> SEQUENCE: 8

```
ctctagttat taatagtaat caattacggg gtcattagtt catagcccat atatggagtt    60
```

```
ccgcgttaca taacttacgg taaatggccc gcctggctga ccgcccaacg accccgccc      120 attgacgtca ataatgacgt atgttcccat agtaacgcca atagggactt tccattgacg     180
tcaatgggtg gagtatttac ggtaaactgc ccacttggca gtacatcaag tgtatcatat     240
gccaagtacg cccccctattg acgtcaatga cggtaaatgg cccgcctggc attatgccca    300
gtacatgacc ttatgggact ttcctacttg gcagtacatc tacgtattag tcatcgctat     360
taccatgcat ggtcgaggtg agccccacgt tctgcttcac tctccccatc tccccccct     420 ccccaccccc aattttgtat ttatttattt tttaattatt ttgtgcagcg atggggggcgg    480 ggggggggg gggcgcgcg ccaggcgggg cgggcgggg cgaggggcgg ggcggggcga       540
ggcggagagg tgcggcggca gccaatcaga gcggcgcgct ccgaaagttt cctttatgg    600 cgaggcggcg gcgcggcgg ccctataaaa agcgaagcgc gcggcgggcg ggagtcgtgc     660
gcgctgcctt cgccccgtgc cccgctccgc cgccgcctcg cgccgcccgc cccggctctg    720
actgaccgcg ttactcccac aggtgagcgg gcgggacggc ccttctcctt cgggctgtaa    780
ttagcgcttg gtttaatgac ggcttgtttc ttttctgtgg ctgcgtgaaa gccttgaggg    840
gctccgggag ggccctttgt gcgggggggag cggctcgggg ctgtccgcgg ggggacggct    900
gccttcgggg gggacgggc agggcggggt tcggcttctg gcgtgtgacc ggcggctcta    960
gagcctctgc taaccatgtt catgccttct tctttttcct acagctcctg ggcaacgtgc    1020
tggttattgt gctgtctcat cattttggca aagaattgga tcggaccgga atcataaaa    1080 aattatttgc tttgtgagcg gataacaatt ataatagatt caattgaggc ctcgaccacc    1140 gggacccttta attcaaccca acacaatata ttatagttaa ataagaatta ttatcaaatc    1200
atttgtatat taattaaaat actatactgt aaattacatt ttatttacaa tcaaaggaga    1260
tataccatgg cgatatcccg ggagctcgtg gatccgaatt ctcagatctc ggcgcgcctg    1320
caggtcgacg gtaccggttc gaagcttgcg gccgcacagc tgtatacacg tgcaagccag    1380
ccagaactcg ccccggaaga ccccgaggat ctcgagcacc accatcacca tcaccatcac    1440
taagtgatta acctcaggtg caggctgcct atcagaaggt ggtggctggt gtggccaatg    1500
ccctggctca caaataccac tgagatcgat ctttttccct ctgccaaaaa ttatggggac    1560
atcatgaagc cccttgagca tctgacttct ggctaataaa ggaaatttat tttcattgca    1620
atagtgtgtt ggaattttt gtgtctctca ctcggaagga catatgggag gcaaatcat    1680 ttaaaacatc agaatgagtt tttggtttag agtttggcaa catatgccca tatgtaacta    1740
gcataacccc ttgggcctc taaacgggtc ttgaggggtt ttttgctgaa agcatgcgga    1800
ggaaattctc cttgaagttt ccctggtgtt caaagtaaag gagtttgcac cagacgcacc    1860
tctgttcact ggtccggcgt attaaaacac gatacattgt tattagtaca tttattaagc    1920
gctagattct gtgcgttgtt gatttacaga caattgttgt acgtattta ataattcatt    1980 aaatttataa tctttagggt ggtatgttag agcgaaaatc aaatgatttt cagcgtcttt    2040
atatctgaat ttaaatatta atcctcaat agatttgtaa aataggtttc gattagtttc    2100
aaacaagggt tgttttccg aaccgatggc tggactatct aatggatttt cgctcaacgc    2160
cacaaaactt gccaaatctt gtagcagcaa tctagctttg tcgatattcg tttgtgtttt    2220
gttttgtaat aaaggttcga cgtcgttcaa atatatgc gctttgtat ttctttcatc      2280 actgtcgtta gtgtacaatt gactcgacgt aaacacgtta atagagctt ggacatattt    2340 aacatcgggc gtgttagctt tattaggccg attatcgtcg tcgtcccaac cctcgtcgtt    2400
agaagttgct tccgaagacg attttgccat agccacacga cgcctattaa ttgtgtcggc    2460
```

```
taacacgtcc gcgatcaaat ttgtagttga gcttttggga attatttctg attgcgggcg    2520 ttttgggcg ggtttcaatc taactgtgcc cgattttaat tcagacaaca cgttagaaag    2580
cgatggtgca ggcggtggta acatttcaga cggcaaatct actaatggcg gcggtggtgg    2640
agctgatgat aaatctacca tcggtggagg cgcaggcggg gctggcggcg gaggcggagg    2700
cggaggtggt ggcggtgatg cagacggcgg tttaggctca aatgtctctt taggcaacac    2760
agtcggcacc tcaactattg tactggtttc gggcgccgtt tttggtttga ccggtctgag    2820
acgagtgcga ttttttttcgt ttctaatagc ttccaacaat tgttgtctgt cgtctaaagg    2880
tgcagcgggt gaggttccg tcggcattgg tggagcgggc ggcaattcag acatcgatgg    2940
tggtggtggt ggtggaggcg ctggaatgtt aggcacggga aaggtggtg gcggcggtgc    3000 cgccggtata atttgttctg gtttagtttg ttcgcgcacg attgtgggca ccggcgcagg    3060
cgccgctggc tgcacaacgg aaggtcgtct gcttcgaggc agcgcttggg gtggtggcaa    3120
ttcaatatta taattggaat acaaatcgta aaaatctgct ataagcattg taatttcgct    3180
atcgtttacc gtgccgatat ttaacaaccg ctcaatgtaa gcaattgtat tgtaaagaga    3240
ttgtctcaag ctcggaacgc tgcgctcggt cgttcggctg cggcgagcgg tatcagctca    3300
ctcaaaggcg gtaatacggt tatccacaga atcagggat aacgcaggaa agaacatgtg    3360
agcaaaaggc cagcaaaagg ccaggaaccg taaaaaggcc gcgttgctgg cgttttccca    3420
taggctccgc cccctgacga gcatcacaaa aatcgacgct caagtcagag gtggcgaaac    3480
ccgacaggac tataaagata ccaggcgttt ccccctggaa gctccctcgt gcgctctcct    3540
gttccgaccc tgccgcttac cggatacctg tccgcctttc tcccttcggg aagcgtggcg    3600
ctttctcata gctcacgctg taggtatctc agttcggtgt aggtcgttcg ctccaagctg    3660
ggctgtgtgc acgaaccccc cgttcagccc gaccgctgcg ccttatccgg taactatcgt    3720
cttgagtcca acccggtaag acacgactta tcgccactgg cagcagccac tggtaacagg    3780
attagcagag cgaggtatgt aggcggtgct acagagttct tgaagtggtg gcctaactac    3840
ggctacacta gaagaacagt atttggtatc tgcgctctgc tgaagccagt taccttcgga    3900
aaaagagttg gtagctcttg atccggcaaa caaaccaccg ctggtagcgg tggtttttttt    3960 gtttgcaagc agcagattac gcgcagaaaa aaaggatctc aagaagatcc tttgttacca    4020
atgcttaatc agtgaggcac ctatctcagc gatctgtcta tttcgttcat ccatagttgc    4080
ctgactcccc gtcgtgtaga taactacgat acgggagggc ttaccatctg gccccagtgc    4140
tgcaatgata ccgcgagacc cacgctcacc ggctccagat ttatcagcaa taaaccagcc    4200
agccggaagg gccgagcgca gaagtggtcc tgcaacttta tccgcctcca tccagtctat    4260
taattgttgc cgggaagcta gagtaagtag ttcgccagtt aatagtttgc gcaacgttgt    4320
tgccattgct acaggcatcg tggtgtcacg ctcgtcgttt ggtatggctt cattcagctc    4380
cggttcccaa cgatcaaggc gagttacatg atccccccatg ttgtgcaaaa aagcggttag    4440
ctccttcggt cctccgatcg ttgtcagaag taagttggcc gcagtgttat cactcatggt    4500
tatggcagca ctgcataatt ctcttactgt catgccatcc gtaagatgct tttctgtgac    4560
tggtgagtac tcaaccaagt cattctgaga atagtgtatg cggcgaccga gttgctcttg    4620 cccgcgtca atacgggata ataccgcgcc acatagcaga actttaaaag tgctcatcat    4680
tggaaaacgt tcttcggggc gaaaactctc aaggatctta ccgctgttga gatccagttc    4740
gatgtaaccc actcgtgcac ccaactgatc ttcagcatct tttactttca ccagcgtttc    4800
tgggtgagca aaaacaggaa ggcaaaatgc cgcaaaaaag gaataagggg cgacacggaa    4860
```

-continued

```
atgttgaata ctcatactct tccttttca atattattga agcatttatc agggttattg      4920
tctcatgtcc gcgcgtttcc tgcatctttt aatcaaatcc caagatgtgt ataaaccacc      4980
aaactgccaa aaaatgaaaa ctgtcgacaa gctctgtccg tttgctggca actgcaaggg      5040
tctcaatcct atttgtaatt attgaataat aaaacaatta taaatgtcaa atttgttttt      5100
tattaacgat acaaaccaaa cgcaacaaga acatttgtag tattatctat aattgaaaac      5160
gcgtagttat aatcgctgag gtaatattta aaatcatttt caatgattc acagttaatt      5220 tgcgacaata taattttatt ttcacataaa ctagacgcct tgtcgtcttc ttcttcgtat      5280
tccttctctt tttcatttt ctcttcataa aaattaacat agttattatc gtatccatat      5340
atgtatctat cgtatagagt aaatttttg ttgtcataaa tatatatgtc ttttttaatg      5400
gggtgtatag taccgctgcg catagttttt ctgtaattta caacagtgct attttctggt      5460
agttcttcgg agtgtgttgc tttaattatt aaatttatat aatcaatgaa tttgggatcg      5520
tcggttttgt acaatatgtt gccggcatag tacgcagctt cttctagttc aattacacca      5580 tttttagca gcaccggatt aacataactt tccaaaatgt tgtacgaacc gttaaacaaa       5640
aacagttcac ctccctttc tatactattg tctgcgagca gttgtttgtt gttaaaaata      5700
acagccattg taatgagacg cacaaactaa tatcacaaac tggaaatgtc tatcaatata      5760
tagttg                                                                5766
```

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
cccagatcat gtttgagacc t                                               21

<210> SEQ ID NO 10
<211> LENGTH: 19
<212> TYPE: DNA
<213> ORGANISM: Artificial Sequence
<220> FEATURE:
<223> OTHER INFORMATION: Synthetic primer

<400> SEQUENCE: 10
agtccatcac gatgccagt                                                  19

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
aggcctgctg tgaactgact                                                 20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
cctggggtac aacaaggatg                                                 20

```
<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
agggcatcat caatttcgag                                                     20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
acattgccca agtctccaac                                                     20

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
ttggccaagg gagatgttac                                                     20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
agtcacgttt gatggcttcc                                                     20

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
ctcttcgaga agtgcgaggt                                                     20

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
tcgatgtcaa tggtctggaa                                                     20

<210> SEQ ID NO 19
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 19
acgtggcctt gaacaacttc                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
attccagcaa cgactggttc                                              20
```

SENSITIZING AGENTS FOR CANCER THERAPY, METHODS OF USE AND METHODS FOR THE IDENTIFICATION THEREOF

The present application is a national phase application under 35 U.S.C. §371 of International Application No. PCT/CA2010/000569 filed Apr. 12, 2010 which claims priority to U.S. Provisional Application 61/170,145 filed Apr. 17, 2009 and U.S. Provisional Application 61/170,148 filed Apr. 17, 2009 the entire text and figures of which disclosures are incorporated herein by reference without disclaimer.

FIELD OF THE INVENTION

This invention relates to the field of cancer therapy and specifically sensitizing agents for cancer therapy, including, but not limited to, radio and chemotherapy. Also described herein is the novel target UROD (uroporphyrinogen decarboxylase), the down-regulation or inhibition of which results in increased sensitivity to cancer therapies.

BACKGROUND

Head and neck cancer (HNC) is the eighth most common cancer worldwide, with an estimated annual global incidence of approximately 650,000 cases and ~90,000 deaths attributed to this disease per year [1]. HNC comprises a diverse group of tumor types arising from the upper aerodigestive tract, including the lip, nasal and oral cavities, sinuses, pharynx, larynx, and other sites in this anatomical region [2]. The vast majority of HNC diagnoses (>90%) are of squamous epithelial cell origin (oral cavity, pharynx, larynx), and are thus termed head and neck squamous cell carcinomas (HNSCC) [2]. Nasopharyngeal carcinoma (NPC) is a less common distinct HNC in that >90% of cases harbor latent Epstein-Barr virus [3]. At the time of diagnosis, ~30-40% of HNC patients typically have localized disease, >50% have associated regional disease, and ~10% harbor distant metastases. In addition to the anatomic and molecular heterogeneity of HNC, most patients present with locally advanced disease, and/or suffer from other co-morbidities, rendering HNC particularly challenging to treat. Despite the advances in therapeutic options over the recent few decades, treatment toxicities and overall clinical outcomes have remained disappointing [4]. For all sites and stages in the head and neck region, 5-year survival rates average ~50% [5].

Radiation therapy (RT) remains the primary curative modality for HNC. Even the most effective RT regimens achieve local control rates of 45-55%, with disease-free survival rates of only 30-40% for patients with locally advanced head and neck squamous-cell carcinomas (HNSCC) [6]. Furthermore, standard RT administering the maximal tolerable dose, limited by the surrounding critical normal tissues, yet is still associated with significant morbidity. Thus, the development of novel strategies to enhance tumor cell killing, while minimizing damage to surrounding normal cells, is critical to improving the therapeutic ratio of RT. The benefits of chemotherapy or molecularly-targeted agents combined with RT for HNC is strongly supported through the results from randomized trials and meta-analyses [7, 8]. However, these results remain modest; meta-analyses have documented concurrent RT with chemotherapy to offer an absolute survival advantage of only 4.5% at 5 years [7]. The 5-year overall survival rate of HNSCC patients treated with both RT and Cetuximab is still only 45.6% [8], underscoring a continued need for further improvement.

Novel molecular therapies for HNC have been developed and evaluated, ranging from adenovirus-mediated gene therapy [9-11] to anti-sense oligonucleotide (ASO) approaches involving systemically delivered Bcl-2 ASO combined with local tumor RT [12]. More recently, a rapid, cell-based phenotype-driven high-throughput screen (HTS) was developed for the large-scale identification of novel HNC cytotoxics, preferably with radiosensitizing activities [13, 14].

Ionizing radiation (IR) induces a myriad of physico-chemical changes at the cellular and molecular level [15], most of which have not yet been clearly elucidated, suggesting the existence of many unidentified radiosensitizing targets.

SUMMARY OF INVENTION

In accordance with one aspect, there is provided a method for sensitizing a subject with cancer to a cancer therapy comprising administering to the subject a sensitizing amount of an agent that downregulates or inhibits UROD.

Preferably, the cancer is a head and neck cancer and the cancer therapy is one of radiation therapy and chemotherapy.

In accordance with a further aspect, there is provided a method for sensitizing a subject with cancer to a cancer therapy comprising downregulating or inhibiting UROD in cancer cells of the subject.

In accordance with a further aspect, there is provided use of an agent that downregulates or inhibits UROD for sensitizing a subject to a cancer therapy.

In accordance with a further aspect, there is provided use of an agent that downregulates or inhibits UROD in the preparation of a medicament for sensitizing a subject to a cancer therapy.

In accordance with a further aspect, there is provided a compound for sensitizing a subject with cancer to a cancer therapy comprising a UROD inhibitor or UROD downregulator.

In accordance with a further aspect, there is provided a method for identifying an agent that sensitizes a subject with cancer to a cancer therapy comprising screening for a compound that downregulates or inhibits UROD.

In accordance with a further aspect, there is provided a method of prognosticating a survival outcome to a cancer therapy of a subject with cancer comprising:
  providing a sample comprising cancer cells from the subject; and
  determining the level of UROD expression and/or activity in the cancer cells;
  wherein a relatively low level of UROD expression and/or activity compared to a control is correlated with an improved clinical outcome in response to cancer therapy.

In accordance with a further aspect, there is provided a method of diagnosing a subject with cancer comprising:
  providing a sample from the subject; and
  assaying the level of UROD expression and/or activity in the sample;
  wherein a relatively high level of UROD expression and/or activity compared to a control is correlated with cancer.

In accordance with a further aspect, there is provided a kit for diagnosing a cancer in or prognosticating a survival outcome to a cancer therapy of a subject with the cancer, comprising an assay for UROD expression and/or activity along with instructions for use.

In accordance with a further aspect, there is provided a method for sensitizing a subject with cancer to a cancer therapy comprising elevating the intracellular iron in cancer cells of the subject.

In accordance with a further aspect, there is provided a method for sensitizing a subject with cancer to a cancer therapy comprising administering an agent that elevates intracellular iron.

In accordance with a further aspect, there is provided a use of an agent that elevates the intracellular iron in cancer cells for sensitizing a subject to a cancer therapy.

In accordance with a further aspect, there is provided a use of an agent that elevates the intracellular iron in cancer cells in the preparation of a medicament for sensitizing a subject to a cancer therapy.

In accordance with a further aspect, there is provided a compound for sensitizing a subject with cancer to a cancer therapy comprising an elevator of intracellular iron.

BRIEF DESCRIPTION OF THE FIGURES

Embodiments of the invention may best be understood by referring to the following description and accompanying drawings. In the drawings.

DETAILED DESCRIPTION

Figure 1:
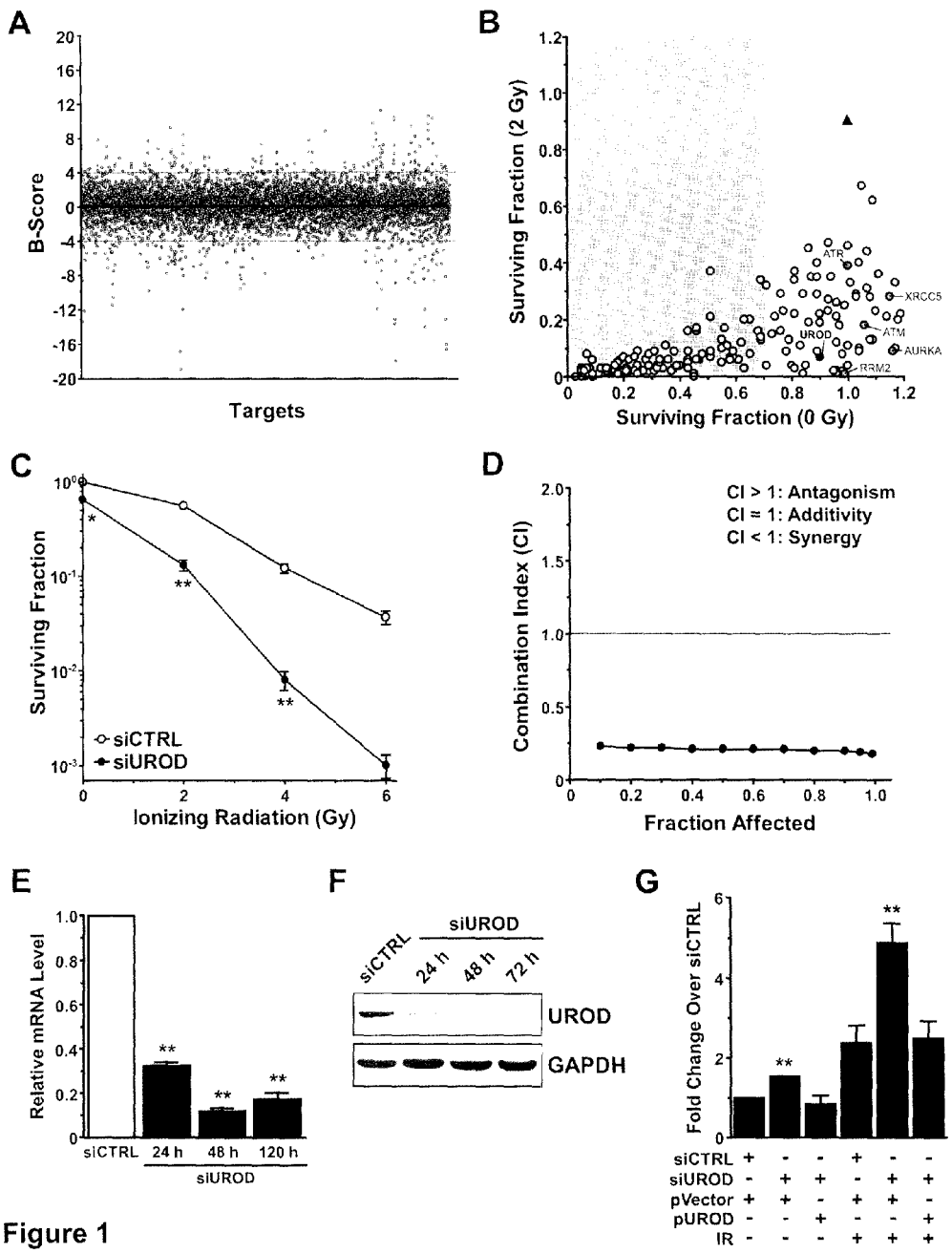
FIG. 1 shows the identification of UROD as a novel radiosensitizing target via a siRNA-based high-throughput screen. (A) Preliminary screen of the Human siGENOME Druggable (6080 genes) and Protein Kinase (800 genes) siRNA Libraries at 2 Gy in transfected FaDu (human hypopharyngeal squamous cell cancer) cells. (B) 67 target sequences with potential radiosensitizing effects (>50% reduction in surviving fraction at 2 Gy vs. 0 Gy) were identified. Targets that decreased the surviving fraction by >30% in the absence of IR were not considered (grey box). Known radiosensitizing targets (grey circles); UROD (black circle); scrambled siRNA control (black triangle). (C) Clonogenic survival curves of FaDu cells transfected with scrambled control siRNA (siCTRL) or UROD siRNA (siUROD) for 48 h, then irradiated (0-6 Gy). Colonies were counted 12 days post-IR. *$p<0.05$ and $p<0.01$, siCTRL vs. siUROD for each IR dose. (D) As in (C), but FaDu cells were transfected with a range of siRNA concentrations (0-60 nM), combined with IR (0-6 Gy) for Chou-Talalay combination index analyses. (E) Relative UROD mRNA levels in FaDu cells transfected with siCTRL or siUROD for 24, 48, and 120 h, as measured by qRT-PCR. $p<0.01$, siCTRL vs. siUROD. (F) UROD protein expression was detected by immunoblotting at 24-72 h post-transfection. (G) FaDu cells were co-transfected with siRNA (siCTRL or siUROD) and plasmid DNA (empty vector control, pVector or siRNA-resistant rescue plasmid, pUROD) for 48 h, and then irradiated (4 Gy). Apoptotic fractions were assessed by flow cytometry 72 h post-IR. **$p<0.01$, siCTRL-pVector vs. siUROD-pVector or siUROD-pUROD±IR. Each datum represents the mean±SEM from three independent experiments.

In the following description, numerous specific details are set forth to provide a thorough understanding of the invention. However, a person skilled in the art would understand when the invention may be practiced without certain specific details. Some methods herein have been described as a series of steps and a person skilled in the art will also understand that the steps may be performed in any logical order unless the context dictates otherwise.

Head and neck cancer (HNC) is a challenging disease due to its heterogeneity and complexity, often resulting in poor survival rates. Radiation therapy (RT) remains the primary curative modality for HNC. Even the most effective RT regimens however, achieve local control rates of 45-55%, with disease-free survival rates of only 30-40%. Thus, the development of novel strategies to enhance tumor cell killing, while minimizing damage to the surrounding normal tissues, is critical to improving cure rates with RT.

A siRNA-based high-throughput screen (HTS) was developed for the large-scale identification of novel genes that will selectively sensitize HNC cells to radiation. The preliminary screen identified 188 target sequences with potential radiosensitizing effects; the validity of the screen was corroborated by the identification of known radiosensitizing targets (e.g. ATM, ATR, Aurora-A kinase). To confirm the initial HTS results, FaDu cells (human hypopharyngeal squamous cell cancer) were transfected with the 188 siRNAs±RT, and those that were cytotoxic without RT were eliminated, leaving 67 potential 'hits'. Targets reducing surviving fraction by >50% at 2 Gy relative to their un-irradiated counterparts were selected. Corroboration of siRNA-mediated mRNA and protein knockdown were assessed using qRT-PCR and Western blotting, respectively.

A key regulator of the heme biosynthetic pathway, uroporphyrinogen decarboxylase (UROD), was thus identified as a potent radiosensitizer. Increased heme biosynthesis has previously been reported in tumor tissues with up-regulation of several regulatory proteins, including UROD. The broad applicability of this radiosensitization was exhibited in other HNC cell lines (nasopharyngeal and laryngeal squamous cancers), as well as other cancer models (cervix, breast, lung, and prostate carcinomas); no radiosensitization was observed in normal oral cavity or oropharyngeal epithelial cells.

Functional validation studies and in vitro characterization of mechanisms for radiosensitization were examined. These studies suggest an effect mediated by tumor-selective enhancement of cellular oxidative stress via perturbation of iron homeostasis and increased reactive oxygen species (ROS) production. In vivo validation studies such as tumor formation assays and treatment of established HNC xenograft models were also evaluated. The clinical relevance of UROD down-regulation in head and neck cancer was also demonstrated.

UROD knockdown has significant implications in the management of human cancers. Its over-expression is able to prognosticate for radiation resistance, thereby potentially allowing selection of cancer patients who would be suitable for siUROD radiosensitization. The therapeutic application of this approach is broad, and effective in the selective enhancement of radiation-induced cytotoxicity in cancer tissues, with no toxicity observed in normal tissues. Furthermore, there is a naturally occurring state of porphyria cutanea tarda (PCT), which is non-lethal; hence a "temporary" state of PCT would have minimal consequences to cancer patients during the few weeks of RT and/or chemotherapy. This discovery uncovers the translational significance of iron homeostasis and dysregulation within the context of tumor radiosensitization, warranting further investigations into this important biological process.

Therefore, in accordance with one aspect, there is provided a method for sensitizing a subject with cancer to a cancer therapy comprising administering to the subject a sensitizing amount of an agent that downregulates or inhibits UROD. Preferably, the cancer is a head and neck cancer and is selected from the group consisting of cancers originating from the lip, nasal and oral cavities, sinuses, pharynx, larynx, and other sites in this anatomical region.

In an embodiment, the cancer is selected from the group consisting of hypopharyngeal carcinoma, nasopharyngeal carcinoma, laryngeal carcinoma, lung adenocarcinoma, cervical carcinoma, prostate carcinoma and mammary adenocarcinoma.

In accordance with a further aspect, there is provided a method for sensitizing a subject with cancer to a cancer therapy comprising downregulating or inhibiting UROD in cancer cells of the subject.

In accordance with a further aspect, there is provided use of an agent that downregulates or inhibits UROD for sensitizing a subject to a cancer therapy.

In accordance with a further aspect, there is provided use of an agent that downregulates or inhibits UROD in the preparation of a medicament for sensitizing a subject to a cancer therapy.

In accordance with a further aspect, there is provided a compound for sensitizing a subject with cancer to a cancer therapy comprising a UROD inhibitor or UROD downregulator.

In accordance with a further aspect, there is provided a method for identifying an agent that sensitizes a subject with cancer to a cancer therapy comprising screening for a compound that downregulates or inhibits UROD.

In accordance with a further aspect, there is provided a method of prognosticating a survival outcome to a cancer therapy of a subject with cancer comprising:
  providing a sample comprising cancer cells from the subject; and
  determining the level of UROD expression and/or activity in the cancer cells;
  wherein a relatively low level of UROD expression and/or activity compared to a control is correlated with an improved clinical outcome in response to cancer therapy.

In accordance with a further aspect, there is provided a method of diagnosing a subject with cancer comprising:
  providing a sample from the subject; and
  assaying the level of UROD expression and/or activity in the sample;
  wherein a relatively high level of UROD expression and/or activity compared to a control is correlated with cancer.

In accordance with a further aspect, there is provided a kit for diagnosing a cancer in or prognosticating a survival outcome to a cancer therapy of a subject with the cancer, comprising an assay for UROD expression and/or activity along with instructions for use.

In accordance with a further aspect, there is provided a method for sensitizing a subject with cancer to a cancer therapy comprising elevating the intracellular iron in cancer cells of the subject.

In accordance with a further aspect, there is provided a method for sensitizing a subject with cancer to a cancer therapy comprising administering an agent that elevates intracellular iron.

In accordance with a further aspect, there is provided a use of an agent that elevates the intracellular iron in cancer cells for sensitizing a subject to a cancer therapy.

In accordance with a further aspect, there is provided a use of an agent that elevates the intracellular iron in cancer cells in the preparation of a medicament for sensitizing a subject to a cancer therapy.

In accordance with a further aspect, there is provided a compound for sensitizing a subject with cancer to a cancer therapy comprising an elevator of intracellular iron.

In preferable embodiments, the cancer therapy is radiation therapy. In one embodiment, the radiation therapy is therapy using ionizing radiation. In another embodiment, the radiation therapy is therapy using non-ionizing radiation and is preferably photodynamic therapy.

In other embodiments, the cancer therapy is chemotherapy. Preferably, the chemotherapy uses Cisplatin, 5-FU or Paclitaxel.

In some embodiments, the agent is any one of an siRNA, antisense oligonucleotide, miRNA, aptamer, protein, shRNA and small molecule, that downregulates or inhibits UROD or a modified version of any of the foregoing.

The term "radiation therapy" is used interchangeably with the term "radiotherapy". In some embodiments, the radiation is one of x-ray and gamma ray. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma ray emitting radioisotopes, such as radioactive isotopes of radium, cobalt and other elements may also be administered to expose tissues to radiation. However, any radiation therapy protocol can be used depending upon the type of cancer to be treated. Radiation therapy as used herein includes both ionizing and non-ionizing radiation. Non-ionizing radiation may be used, for example, in connection with photodynamic therapy ("PDT") and PDT-photosensitizing agents.

The term "chemotherapy" refers to the use of drugs to treat cancer. A "chemotherapeutic agent" is used to connote a compound or composition that is administered in the treatment of cancer. Some examples of chemotherapeutic agents include, but are not limited to, antibiotic chemotherapeutics such as, Doxorubicin, Daunorubicin, Mitomycin (also known as mutamycin and/or mitomycin-C), Actinomycin D (Dactinomycin), Bleomycin, Plicomycin; plant alkaloids such as Taxol, Vincristine, Vinblastine; miscellaneous agents such as Cisplatin, VP16, Tumor Necrosis Factor; alkylating agents such as, Carmustine, Melphalan (also known as alkeran, L-phenylalanine mustard, phenylalanine mustard, L-PAM, or L-sarcolysin, is a phenylalanine derivative of nitrogen mustard), Cyclophosphamide, Chlorambucil, Busulfan (also known as myleran), Lomustine; and other agents for example, Cisplatin (CDDP), Carboplatin, Procarbazine, Mechlorethamine, Camptothecin, Ifosfamide, Nitrosurea, Etoposide (VP16), Tamoxifen, Raloxifene, Estrogen Receptor Binding Agents, Gemcitabine, Navelbine, Farnesyl-protein transferase inhibitors, Transplatinum, 5-Fluorouracil, and Methotrexate, Temazolomide (an aqueous form of DTIC), or any analog or derivative variant of the foregoing.

As used herein, "UROD" refers to Uroporphyrinogen decarboxylase enzyme or gene as the context dictates. UROD is an enzyme in the heme biosynthetic pathway, catalyzing the decarboxylation of uroporphyrinogen to form coproporphyrinogen and four molecules of carbon dioxide.

The term "oligonucleotide" as used herein refers to a nucleic acid molecule comprising from about 1 to about 100 nucleotides, more preferably from 1 to 80 nucleotides, and even more preferably from about 4 to about 35 nucleotides. This may include nucleic acid molecules of variable length that correspond either to the sense strand or to the non-coding strand of a target nucleic acid sequence.

"Antisense oligonucleotides" (AON) are complementary to a region of a target gene and are capable of hybridizing to the target gene sequence and inhibiting gene expression. Gene expression is inhibited through hybridization of an AON to a specific messenger RNA (mRNA) sense target according to the Watson-Crick base pairing, typically in which adenosine and thymidine (uracil in mRNA) or guanosine and cytidine interact through hydrogen bonding. Without being bound to any theory, two mechanisms are generally thought to account for these effects, the first being hybridization with impaired translation of targeted mRNA, the second being the induction of RNase H or similar enzymes with associated degradation of target mRNA. Oligonucleotide compounds in accordance with the present invention also include siRNAs (small interfering RNAs) and the RISCs (RNA-induced silencing complexes) containing them that result from the RNAi (RNA interference) approach. The RNAi approach is a tool for the inhibition of target gene expression. RNAi is based on an ancient anti-viral defense mechanism in lower eukaryotes. It is induced by double-stranded RNA and its processing to typically 21-23 nt siRNAs, which cause the degradation of homologous endogenous mRNA after hybridizing to the target mRNA in a single stranded fashion with the assistance of the RISC complex. The way in which RNAi inhibits target gene expression remains to be fully elucidated, but presently, RNAi serves as an attractive choice approach to generate loss-of-function phenotypes across a broad spectrum of eukaryotic species, such as nematodes, flies, plants, fungi and mammals.

Oligonucleotide compounds in accordance with the present invention also include microRNA (miRNA). "MicroRNA" are single-stranded RNA molecules, typically of about 21-23 nucleotides in length, which regulate gene expression in a hybridization dependent manner. Typically, miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, typically at the 3' end of the mRNA, and their main function is to downregulate gene expression.

As used herein, the term "aptamer," e.g., RNA aptamer or DNA aptamer, includes single-stranded oligonucleotides that bind specifically to a target molecule. Aptamers are selected, for example, by employing an in vitro evolution protocol called systematic evolution of ligands by exponential enrichment. Aptamers bind tightly and specifically to target molecules; most aptamers to proteins bind with a $K_d$ (equilibrium dissociation constant) in the range of 1 pM to 1 nM. Aptamers and methods of preparing them are described in, for example, E. N. Brody et al. (1999) Mol. Diagn. 4:381-388.

In one embodiment, the subject aptamers can be generated using SELEX, a method for generating very high affinity receptors that are composed of nucleic acids instead of proteins. See, for example, Brody et al. (1999) Mol. Diagn. 4:381-388. SELEX offers a completely in vitro combinatorial chemistry alternative to traditional protein-based antibody technology. Similar to phage display, SELEX is advantageous in terms of obviating animal hosts, reducing production time and labor, and simplifying purification involved in generating specific binding agents to a particular target PET.

An "amino acid" is a monomer unit of a peptide, polypeptide, or protein. There are twenty amino acids found in naturally occurring peptides, polypeptides and proteins, all of which are L-isomers. The term also includes analogs of the amino acids and D-isomers of the protein amino acids and their analogs.

A "protein" is any polymer consisting essentially of any of the 20 amino acids. Although "polypeptide" is often used in reference to relatively large polypeptides, and "peptide" is often used in reference to small polypeptides, usage of these terms in the art overlaps and is varied. The term "protein" as used herein refers to peptides, proteins and polypeptides, unless otherwise noted.

The term "small molecule" is a term of the art and includes molecules that are less than about 1000 molecular weight or less than about 500 molecular weight. Exemplary small molecule compounds which can be screened for activity include, but are not limited to, peptides, peptidomimetics, nucleic acids, carbohydrates, small organic or inorganic molecules, and natural product extract libraries.

The term "downregulate" is used herein to refer to at least partial inhibition or knockdown of the expression of a gene or activity of the protein that it encodes. For example, in some embodiments, an antisense oligonucleotide, siRNA or miRNA compound exhibiting complementarity to UROD downregulates or inhibits expression of UROD in a hybridization dependent manner. In another embodiment an aptamer, protein or small molecule downregulates or inhibits UROD protein activity by binding thereto.

As used herein, the term "screening" or "to screen" refers to a process in which a large number of potentially useful agents are processed in the methods of the invention. Without limitation, screening may refer to an assay of members having a desired activity or function from a library such as small molecule, aptamer, protein and nucleic acid libraries. For example, in some embodiments, potential antisense oligonucleotides, siRNAs and/or miRNAs exhibiting complementarity to UROD are screened/processed in order to identify species that downregulate or inhibit expression of UROD in a hybridization dependent manner. In another embodiment aptamers, proteins and/or small molecules are screened/processed to identify species that downregulate or inhibit UROD protein activity by binding thereto.

The term "sensitizing amount" means a sufficient amount of an agent to provide the desired sensitizing effect. For example, in some embodiments, "sensitizing amount" means that dose of agent effective to increase the sensitivity of cancerous cells or tumour to radiation therapy or chemotherapy.

The term "prognosticating" as used herein means predicting or identifying the clinical outcome group that a subject belongs to according to the subject's similarity to a control group or control profile.

The term "diagnosing" means judging, predicting, assessing and/or evaluating as well as identifying and characterizing, including screening, whether a person is susceptible of or suffers from cancer, including, but not limited to head and neck cancers.

The term "sample" as used herein refers to any fluid, cell or tissue sample from a subject, which can be assayed, for example, for UROD expression or activity.

As used herein, the term "control" refers to a specific value or dataset that can be used to prognosticate, diagnose or classify the value e.g. expression level of UROD obtained from the test sample associated with an outcome class (e.g. high vs. low survival or tumour vs. normal cells). A person skilled in the art will appreciate that the comparison between the expression of UROD in the test sample and the expression of UROD in the control will depend on the control used. In some embodiments, the control comprises an UROD expression profile from multiple samples in order to dichotomize the control values into different outcome classes (e.g. high vs. low survival or tumour vs. normal cells). As such, when a test sample is compared to the UROD expression profile, the test sample can be placed in one of the outcome classes based on UROD expression.

EXAMPLES

Materials and Methods

Cell Lines

FaDu, A549, SiHa, ME-180, T47D, DU-145, and MRC5 cells were obtained from the American Type Culture Collection (Manassas, Va.). Normal human oropharyngeal (NOP) and oral epithelial (NOE) cells were purchased from Celprogen (San Pedro, Calif.). Untransformed fibroblasts from familial porphyria cutanea tarda (type II) patients (GM01482, GM00977, GM00961, GM01041) and GM05757 (primary normal human skin) fibroblasts were obtained from Coriell Institute (Camden, N.J.). All cell lines were cultured according to the manufacturer's specifications. C666-1 undifferentiated nasopharyngeal cancer cells [16] were maintained in RPMI 1640 supplemented with 10% fetal bovine serum (Wisent, Quebec, Canada) and antibiotics (100 mg/L penicillin and 100 mg/L streptomycin). UTSCC-8 and -42a laryngeal squamous cell cancer cells were a gift from R. Grénman (Turku, Finland) and maintained as previously described [17]. All cells were maintained in 5% $CO_2$, 21% $O_2$, and 95% humidity at 37° C. unless otherwise stated.

Patient Samples

Thirty-eight formalin-fixed paraffin-embedded (FFPE) tissue biopsies from locally advanced HNSCC patients (Stage III or IV; oropharynx, hypopharynx, or larynx primary SCC subsites), who participated in a randomized clinical study of two RT fractionation regimens [18] were utilized with Institutional Research Ethics Board approval. FFPE samples were macro-dissected for regions of invasive SCC (>70% malignant epithelial cell content). Five normal human larynx and tonsillar FFPE tissues were purchased from Asterand (Detroit, Mich.). Total tumor RNA was extracted with Recover-All Total Nucleic Acid Isolation Kit for FFPE (Ambion, Austin, Tex.) as specified by the manufacturer.

Reagents

Cisplatin, 5-fluorouracil, Paclitaxel, δ-aminolevulinic acid hydrochloride, and deferoxamine mesylate salt were obtained from Sigma-Aldrich (St. Louis, Mo.). All compounds were dissolved and/or diluted in complete media.

BrdU-Based siRNA High-Throughput Screen

The Human siGENOME Druggable and Protein Kinase siRNA Libraries (Dharmacon, Lafayette, Colo.) were provided by the Samuel Lunenfeld Research Institute (SLRI) HTS Robotics Facility (Toronto, Canada). Automation of the 96-well siRNA transfection and bromodeoxyuridine (BrdU) cell proliferation assay (Exalpha Biologicals, Shirley, Mass.) were performed using the BioMek FX (Beckman Coulter, Fullerton, Calif.), SpectraMax Plus$^{384}$ microplate reader (Molecular Devices, Sunnyvale, Calif.), and SLRI robotics platform.

Working stock solutions of siRNA were prepared in Opti-MEM I reduced-serum media (Invitrogen, Carlsbad, Calif.). Reverse transfections (final concentration of 40 nM siRNA) were performed with Lipofectamine 2000 (Invitrogen) as specified by the manufacturer. Columns 1 and 2 of each plate contained siRNA targeting DNA ligase IV (LIG4 siGENOME SMARTpool; Dharmacon), serving as the positive radiosensitizing control, and scrambled negative siRNA control (ON-TARGETplus Non-Targeting Pool; Dharmacon), respectively. Twenty-four h post-transfection, 100 µL of complete media was added to each well, then cells were irradiated using a $^{137}$Cs unit (Gammacell 40 Extractor; MDS Nordion, Ottawa, Canada) at a dose rate of 0.84 Gy/min. Cells were incubated for an additional 72 h, at which time, BrdU (Exalpha Biologicals) was added to each well. After 24 h, cells were monitored for BrdU incorporation on a SpectraMax Plus$^{384}$ microplate reader according to the manufacturer's specifications.

Transfections siRNAs targeting UROD (Hs_UROD_2/8 HP GenomeWide siRNAs) and a scrambled control (AllStars Negative Control siRNA) were purchased from Qiagen (Valencia, Calif.). A plasmid vector containing the protein-coding sequence of UROD (Hs_UROD_IM_1 QIAgene Expression Construct) and an empty vector control (pQE-TriSystem Vector) were also purchased from Qiagen. All transfections were performed in complete media without antibiotics using Lipofectamine 2000 and 40 nM of siRNA and/or 1 µg of plasmid DNA.

| Product | Catalogue Number | | Sequence |
|---|---|---|---|
| Hs_UROD_2 siRNA | SI00008162 | Target: | 5'-GACGGTGACATTGCAGGGCAA-3' (SEQ ID NO. 1) |
| | | Sense Strand: | 5'-CGGUGACAUUGCAGGGCAAUU-3' (SEQ ID NO. 2) |
| | | Anti-sense Strand: | 5'-UUGCCCUGCAAUGUCACCGUC-3' (SEQ ID NO. 3) |
| Hs_UROD_8 siRNA | SI05034988 | Target: | 5'-CTCAAGTACCACTAACACAGA-3' (SEQ ID NO. 4) |
| | | Sense Strand: | 5'-CAAGUACCACUAACACAGAUU-3' (SEQ ID NO. 5) |
| | | Anti-sense Strand: | 5'-UCUGUGUUAGUGGUACUUGAG-3' (SEQ ID NO. 6) |

| Product | Catalogue Number | Sequence |
|---|---|---|
| AllStars Negative Control siRNA | 1027281 | Proprietary sequence |
| Hs_UROD_IM_1 QIAgene Expression Construct Plasmid | EIM0140882 | (SEQ ID NO. 7) |
| pQE-TriSystem Vector | 33903 | (SEQ ID NO. 8) |

Quantitative Real-Time PCR (qRT-PCR)

Primers for PCR amplifications were designed using Primer3 software (available on the World Wide Web at primer3.sourceforge.net). Total RNA from transfected cells was harvested using the RNeasy Mini Kit (Qiagen). Total RNA (1 µg) was reverse-transcribed using SuperScript II Reverse Transcriptase (Invitrogen) as specified by the manufacturer. qRT-PCR was performed using SYBR Green PCR Master Mix (Applied Biosystems, Foster City, Calif.), and an ABI PRISM 7900 Sequence Detection System (Applied Biosystems) with cycle parameters previously described [12]. Relative mRNA levels 15 were calculated using the $2^{-\Delta\Delta cT}$ method [19].

mean inactivation dose (D-bar), which represents the area under the survival curve [21]. Radiosensitization was expressed as an enhancement ratio, defined as the mean inactivation doses of control to treatment.

Cell Viability Assay

The CeliTiter 96 $AQ_{ueous}$ One Solution Cell Proliferation Assay (3-(4,5-dimethylthiazol-2-yl)-5-(3-carboxymethoxyphenyl)-2-(4-sulfophenyl)-2H-tetrazolium, inner salt MTS (Promega, Madison, Wis.) was used to detect cell viability according to the manufacturer's specifications.

Flow Cytometric Assays

Flow cytometric analyses were performed on a FACSCalibur Flow Cytometer (BD Biosciences, San Jose, Calif.),

| Gene | Forward Sequence | Reverse Sequence | SEQ ID |
|---|---|---|---|
| β-ACTIN | 5'-CCCAGATCATGTTTGAGACCT-3' | 5'-AGTCCATCACGATGCCAGT-3' | 9/10 |
| UROD | 5'-AGGCCTGCTGTGAACTGACT-3' | 5'-CCTGGGGTACAACAAGGATG-3' | 11/12 |
| SOD1 | 5'-AGGGCATCATCAATTTCGAG-3' | 5'-ACATTGCCCAAGTCTCCAAC-3' | 13/14 |
| SOD2 | 5'-TTGGCCAAGGGAGATGTTAC-3' | 5'-AGTCACGTTTGATGGCTTCC-3' | 15/16 |
| GPX1 | 5'-CTCTTCGAGAAGTGCGAGGT-3' | 5'-TCGATGTCAATGGTCTGGAA-3' | 17/18 |
| FTMT | 5'-ACGTGGCCTTGAACAACTTC-3' | 5'-ATTCCAGCAACGACTGGTTC-3' | 19/20 |

Western Blot Analysis

Total protein extracts from transfected cells were harvested and prepared for immunoblotting as previously described [12]. Membranes were probed with anti-UROD polyclonal (clone L-19; 1:300 dilution; Santa Cruz Biotechnology, Santa Cruz, Calif.) or anti-GAPDH monoclonal (1:15000 dilution; Abcam, Cambridge, Mass.) antibodies, followed by secondary antibodies conjugated to horseradish peroxidase (1:2000 dilution; Abcam). GAPDH protein levels were used as loading controls. Western blots were quantified with the Adobe Photoshop Pixel Quantification Plug-In (Richard Rosenman Advertising & Design, Toronto, Canada).

Colony Formation Assay

Cells were irradiated (0-6 Gy) 48 h post-transfection and harvested immediately for seeding (500-5000 cells/well in 6-well plates). Twelve days later, colonies were fixed in 70% ethanol, stained with 10% methylene blue, and colonies of ≥50 cells were counted. Clonogenic survival curve data were utilized to evaluate the interactive effects of combinatorial therapies via the Chou-Talalay combination index method [20]. Radiosensitivity was also expressed in terms of the equipped with FlowJo software (Tree Star, Ashland, Oreg.). Cell cycle distributions, caspase activation, and mitochondrial membrane potentials were measured as previously described [17]. Intracellular ROS levels were quantified using the non-specific 5-(and 6-)chloromethyl-2',7'-dichlorodihydrofluorescein diacetate (CM-$H_2$DCFDA) dye, and the superoxide-selective dihydroethidium (DE) dye as instructed by the manufacturer (Invitrogen).

γ-H2AX Detection

Global cellular γ-H2AX protein levels were quantified by flow cytometry using the H2AX Phosphorylation Assay Kit (Upstate Biotechnology, Lake Placid, N.Y.) as specified by the manufacturer. To image γ-H2AX nuclear foci, cells transfected on cover slips were fixed with 2% paraformaldehyde (PFA)-0.2% Triton X-100, then probed with anti-γ-H2AX mouse monoclonal antibody (clone JBW301; Upstate Biotechnology), followed by donkey anti-mouse Alexa 488 antibody (Invitrogen) and DAPI (4',6-diamidino-2-phenylindole; Invitrogen) for nuclear staining. Cells were imaged with an Olympus IX81 inverted microscope equipped with a 16-bit Photometrics Cascade 512B EM-CCD camera (Roper Scientific, Tucson, Ariz.).

Hypoxia Treatment

Transfected cells were immediately exposed to a continuous flow of humidified 0.2% $O_2$ with 5% $CO_2$ and balanced $N_2$ (Praxair, Ontario, Canada) in an In Vivo$_2$ 400 Hypoxia Chamber (Ruskinn Technology, Pencoed, UK). An OxyLite 4000 oxygen-sensing probe (Oxford Optronix, Oxford, UK) was used to verify target $O_2$ levels.

Iron Histochemistry

Intracellular $Fe^{2+}$ and $Fe^{3+}$ were detected according to Perl's Prussian blue and Turnbull's blue staining protocols [22], respectively. Images were captured with a Nikon ECLIPSE E600 microscope equipped with a Nikon DXM1200F digital camera (Nikon Instruments, Melville, N.Y.) for quantitative analysis using SimplePCI imaging software (Hamamatsu, Sewickley, Pa.).

Porphyrin Detection

Transfected cells were treated with ALA (500 μM) for 4 h. Cells were lysed with SOLVABLE (PerkinElmer, Waltham, Mass.), and intracellular porphyrin levels were measured spectrofluorometrically using a SpectraMax Plus$^{384}$ microplate reader (excitation 405 nm, emission 635 nm). To visualize porphyrin accumulation, transfected cells±ALA were stained with MitoTracker Green FM (Invitrogen) and Hoechst 33342 (Invitrogen) as specified by the manufacturer. Live cells were imaged on a Zeiss LSM510 confocal microscope (Carl Zeiss MicroImaging).

In Vivo Tumor Model

All animal experiments utilized 6-8 week-old severe combined immunodeficient (SCID) BALB/c female mice in accordance with the guidelines of the Animal Care Committee, Ontario Cancer Institute, University Health Network (Toronto, Canada). TLDs and body weights were recorded thrice weekly; mice were euthanized by $CO_2$ once TLDs reached ~14 mm.

Tumor Formation Assay

Cells transfected with siCTRL or siUROD for 48 h were harvested and implanted into the left gastrocnemius muscle of SCID mice ($2.5\times10^5$ viable cells in 100 μL growth medium per mouse), followed immediately by administration of local tumor RT (4 Gy). Mice were immobilized in a Lucite box and the tumor-bearing leg was exposed to 225 kV (13 mA) at a dose rate of 3.37 Gy/min (X-RAD 225C Biological X-Ray Irradiator; Precision X-Ray, North Branford, Conn.).

Therapeutic Tumor Growth Assay

Cells were implanted into the left gastrocnemius muscle of SCID mice ($2.5\times10^5$ viable cells in 100 μL). Once the TLDs reached an average of ~8 mm, mice were injected intraperitoneally (IP) with 600 pmol of siRNA complexed to in vivo-jetPEI (Polyplus-Transfection, New York, N.Y.), thrice a week for up to 2 weeks. siRNAs were mixed with in vivo-jetPEI following the manufacturer's specifications (nitrogen/phosphate ratio: 8). Local tumor RT (4 Gy) was delivered on days 5 and 13 post IP-injections.

In Vivo Knockdown Validation

To assess the extent of UROD knockdown in vivo, mice were sacrificed 24 h after the last treatment described in Methods (Therapeutic Tumor Growth Assay). Tumors were excised, immediately fixed in 10% formalin for 48 h, 70% alcohol for an additional 48 h, paraffin embedded, and then sectioned (5 μm). Immunohistochemical analysis was performed using microwave antigen retrieval with anti-UROD polyclonal antibody (clone B02; 1:500 dilution; Abnova, Walnut, Calif.) and Level-2 Ultra Streptavidin Detection System (Signet Laboratories, Dedham, Mass.). For immunoblotting, tumors were excised and immediately snap-frozen in liquid nitrogen. 30 mg of tumor tissue was lysed and homogenized as detailed elsewhere [23]; 30 μg of protein was analyzed for UROD expression via immunoblotting as described above.

Statistical Analyses

All experiments were performed at least three independent times, with the data presented as the mean±SEM. Statistical differences between treatment groups were determined using the Student's t test and one-way ANOVA. The Ingenuity Pathways Analysis software (Ingenuity Systems, Redwood City, Calif.) was used to identify functional biological networks from the HTS data. The right-tailed Fisher Exact test was employed to calculate p-values and scores (p-score=−$\log_{10}$ p-value), indicating the likelihood of genes being observed together in a network due to random chance.

Results

Figure 2:
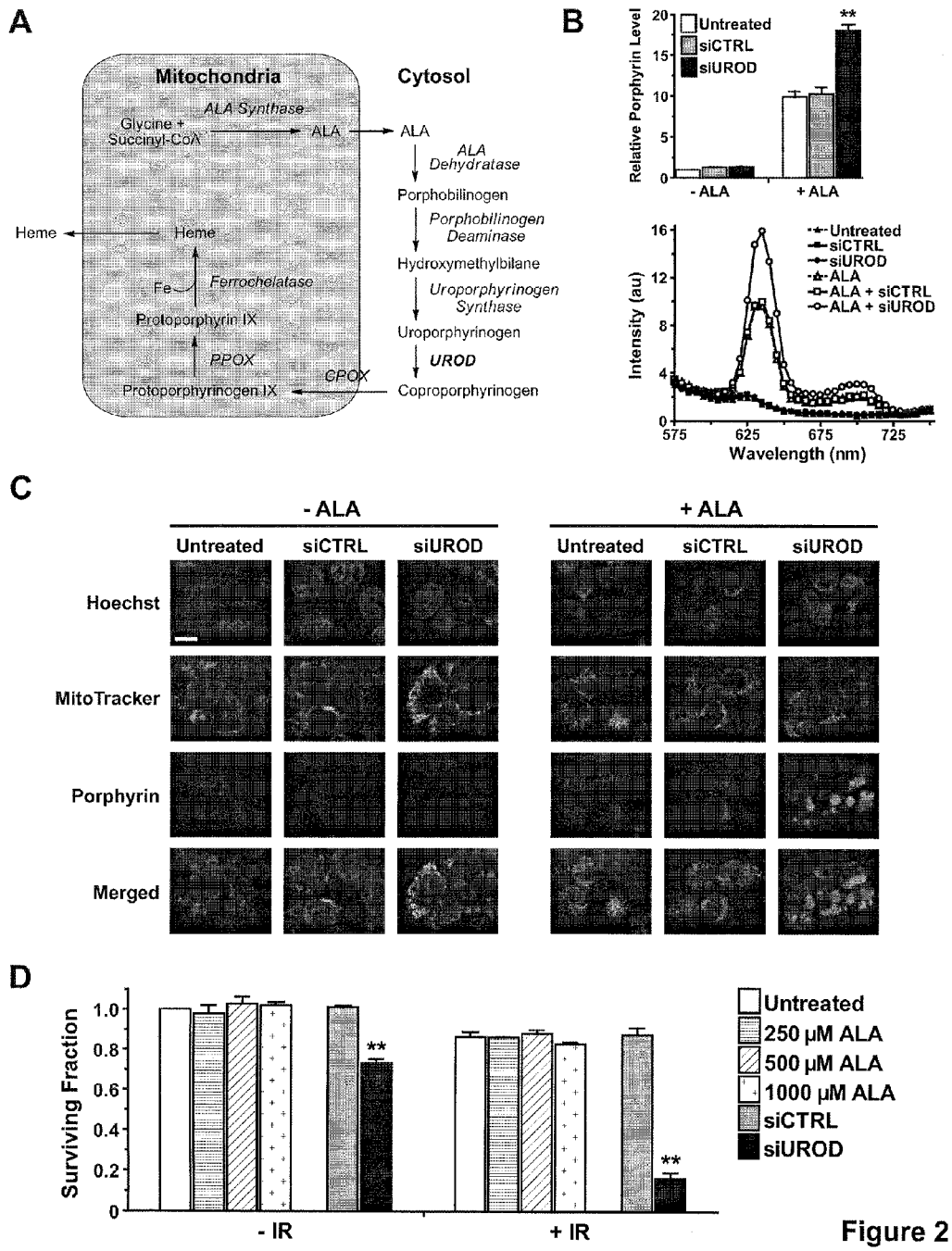
FIG. 2 shows that the radiosensitizing effect of UROD knockdown is independent of porphyrin accumulation. (A) Heme biosynthetic pathway. ALA, δ-aminolevulinic acid; CPOX, coproporphyrinogen oxidase; PPOX, protoporphyrinogen oxidase; Fe, iron. (B) Porphyrin synthesis in mock-, siCTRL-, or siUROD-transfected FaDu cells was artificially induced with ALA (500 µM, 4 h) prior to porphyrin extraction at 24 h post-transfection. Porphyrin levels were quantified spectrofluorometrically and normalized to total cell number. Representative spectral scans (575-750 nm) are shown. $p<0.01$, siUROD vs. siCTRL or untreated±ALA. (C) Fluorescent microscopy images of transfected cells±ALA (500 µM, 1 h). Mitochondria and nuclei were stained with MitoTracker Green and Hoechst 33342, respectively. Intracellular porphyrin excited with a wavelength of ~400 nm emits red fluorescence at a peak of ~635 nm. Scale bar, 10 µm. (D) ALA-treated (250-1000 µM, 4 h) and siCTRL- or siUROD-transfected (48 h-transfection) FaDu cells were irradiated (4 Gy), then cell viability was assessed 96 h later via MTS assay. $p<0.01$, siCTRL vs. siUROD±IR; untreated vs. ALA±IR. In all cases, each datum represents the mean±SEM from three independent experiments.
Figure 6:
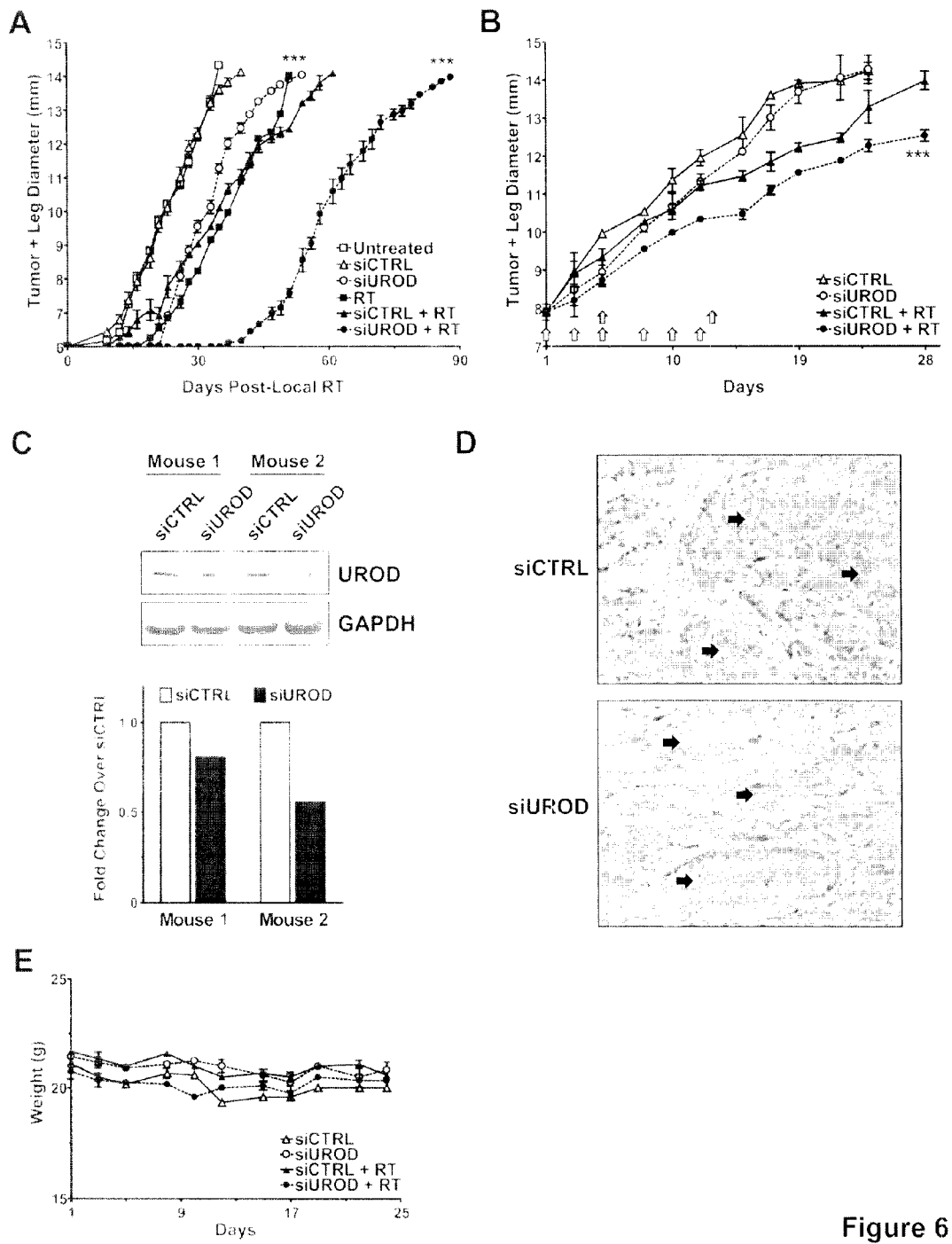
FIG. 6 shows the in vivo efficacy of UROD knockdown plus irradiation in HNC models. (A) Mock, siCTRL, or siUROD-transfected FaDu cells were implanted into the left gastrocnemius muscle of SCID mice, followed immediately by local RT (4 Gy). Each treatment group comprised of 9 mice. *$p<0.001$, siUROD vs. mock or siCTRL±RT. (B) FaDu tumors were established in SCID mice; once TLDs reached ~8 mm, mice were randomly assigned to siCTRL, siUROD, siCTRL-plus-RT, or siUROD-plus-RT. Mice were intraperitoneally-injected with 600 pmol of jetPEI-complexed siRNA thrice a week for up to 2 weeks (white arrows). Local tumor RT (4 Gy) was delivered on days 5 and 13 post IP-injections (grey arrows). Each treatment group comprised of ≥5 mice. *$p<0.001$, siUROD vs. siCTRL+RT. (C) UROD knockdown was assessed in FaDu tumors 24 h after the last treatment as described in (B). Excised tumors were subjected to immunoblotting for UROD expression. Western blots were quantified and relative fold changes in UROD protein levels were determined by normalizing to corresponding GAPDH loading controls, then compared to siCTRL-treated tumors. (D) UROD knockdown in tumors (black arrows) was also verified by immunohistochemistry. (E) Minimal differences in the average mice body weights for each treatment group from (B) indicated that the systemic siUROD-plus-local RT regimen was well-tolerated. Each datum represents the mean±SEM from at least two independent experiments.

We have successfully developed an RNAi-based radiosensitizer HTS (FIG. 1A, B), and identified a heretofore unreported novel radiosensitizing target for the treatment of human HNC. Uroporphyrinogen decarboxylase (UROD) is the fifth enzyme in the heme biosynthetic pathway (FIG. 2A) that catalyses the decarboxylation of uroporphyrinogen to coproporphyrinogen [24]. Our findings reveal a potentially novel function of UROD in tumor response to ionizing radiation, an established anti-cancer treatment modality. Clonogenic survival curves confirmed UROD down-regulation to significantly enhance the radiosensitivity of FaDu cells, a highly aggressive radioresistant HNC cell line, in a dose-dependent and synergistic manner (FIG. 1C,D). Corroboration of siRNA-mediated UROD knockdown was determined via qRT-PCR and immunoblotting (FIG. 1E,F). To ensure this observation was not due to off-target effects, a rescue plasmid expressing target mRNA refractory to siRNA via silent mutations was utilized. Co-transfection of FaDu cells with siUROD and the rescue plasmid completely neutralized any siUROD-mediated effects, with or without IR (FIG. 1G), further confirming a siUROD-specific process. In vivo, siUROD-plus-RT dramatically reduced the tumor-forming capacity of FaDu cells (FIG. 6A), and significantly delayed the growth of established tumors systematically treated with UROD siRNA plus local tumor RT (FIG. 6B); whilst maintaining a favorable toxicity profile (FIG. 6E; no significant difference in mice body weights with these treatments).

UROD down-regulation was functionally validated by measuring overall changes in oxidized porphyrin levels. Spectrofluorometrically, porphyrin accumulation with siUROD alone was negligible (FIG. 2B); thus, FaDu cells were pre-treated with δ-aminolevulinic acid (ALA) to artificially induce porphyrin synthesis. ALA-plus-siUROD significantly increased intracellular porphyrin levels relative to ALA alone or siCTRL-treated cells. Similar observations were made via fluorescent microscopy (FIG. 2C), reflecting the disruption of heme biosynthesis by siUROD. Since the majority of currently utilized photosensitizers in photodynamic therapy (PDT) are porphyrin based [25], it was of interest to compare the radiosensitizing effects of siUROD to commonly used photosensitizers. ALA-based PDT is a well established anti-cancer therapy that utilizes the heme precursor ALA, to induce accumulation of protoporphyrin IX (PPIX) in neoplastic cells [26, 27]. When ALA-treated cells are exposed to visible light, PPIX become excited and induce ROS formation, leading to oxidative stress-mediated cell death. In this study, siUROD-plus-IR was dramatically more cytotoxic compared to the negligible effects of ALA-plus-IR (FIG. 2D), indicating that the effects of siUROD were independent of intracellular porphyrin accumulation (FIG. 2B,C), thus distinct from PDT.

Figure 4:
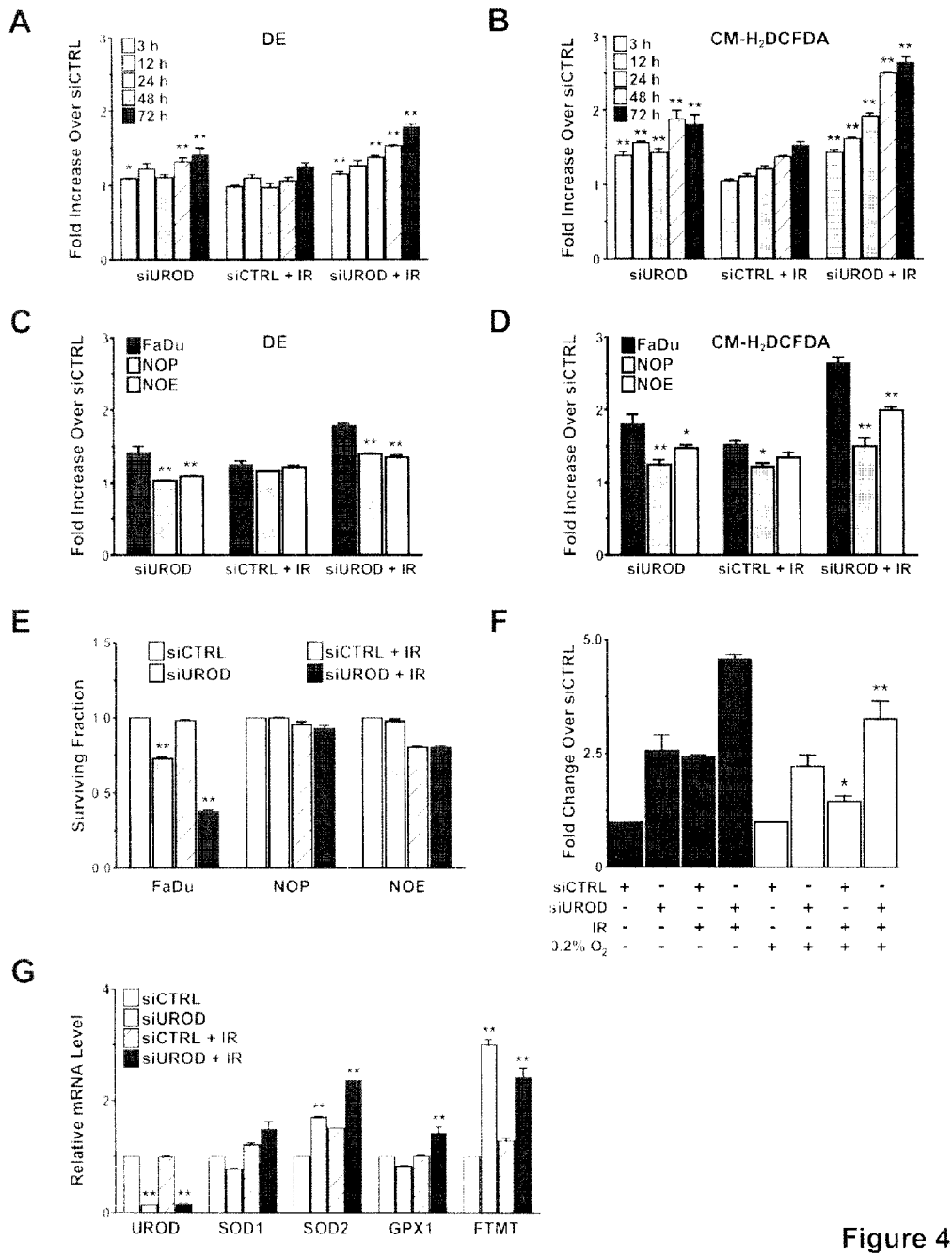
FIG. 4 shows that siUROD-mediated radiosensitization enhances cellular oxidative stress. (A) Intracellular superoxide anions in siCTRL- or siUROD-transfected FaDu cells at 3-72 h post-IR (4 Gy) were detected by flow cytometry with dihydroethidium (DE). *$p<0.05$ and **$p<0.01$, siCTRL vs. siUROD±IR at each time point. (B) Overall ROS levels in transfected FaDu cells were measured with CM-H$_2$DCFDA at 3-72 h post-IR (4 Gy). *$p<0.05$ and $p<0.01$, siCTRL vs. siUROD±IR at each time point. (C) Superoxide radical levels in two transfected normal head and neck epithelial cells (NOP, normal oropharyngeal; NOE, normal oral epithelial) 72 h post-IR (4 Gy). $p<0.01$, normals vs. FaDu at 72 h post-IR. (D) Overall ROS levels in transfected NOP and NOE cells 72 h post-IR (4 Gy). *$p<0.05$ and $p<0.01$, normals vs. FaDu at 72 h post-IR. (E) Cell viability of siCTRL or siUROD-transfected FaDu, NOP, and NOE cells at 96 h post-IR (2 Gy) via MTS assay. $p<0.01$, siCTRL vs. siUROD±IR. (F) FaDu cells were transfected with siCTRL or siUROD and irradiated under normoxia (21% O$_2$) or hypoxia (0.2% O$_2$). Apoptotic fractions were assessed by flow cytometry 72 h post-IR. *$p<0.05$ and $p<0.01$, normoxic vs. hypoxic treatments. (G) Relative mRNA expression of a panel of genes involved in cellular oxidative stress responses in siCTRL- or siUROD-transfected FaDu cells 48 h post-IR. Relative fold changes represent average ΔCt values normalized to those of β-actin, then compared to siCTRL-transfected cells. $p<0.01$, siCTRL vs. siUROD±IR. Each datum represents the mean±SEM from three independent experiments.

Although PDT and our siUROD radiosensitizing strategy both exploit the heme biosynthesis pathway to harnesses their anti-cancer effects, siUROD is superior for several reasons. Tumor hypoxia severely hampers PDT efficacy, since molecular $O_2$ is a prerequisite for the production of photo-induced singlet oxygen molecules [28, 29]. However, siUROD-plus-IR retained radiosensitizing efficacy even under hypoxic conditions (FIG. 4F). The applicability of PDT is further limited since the light source used to excite porphyrins and its derivatives occupy the visible spectrum, which cannot penetrate tissues>0.8 cm, restricting PDT to superficial lesions [30]. Moreover, porphyrins cannot be excited by the high-energy photons of x-rays or γ-rays [31], thereby accounting for the modest radiosensitizing efficacies of porphyrins [30, 32, 33]. Thus, siUROD provides a clear therapeutic advantage with significant sensitization by γ-rays, a mainstay in the standard anti-cancer therapeutic armamentarium.

Figure 3:
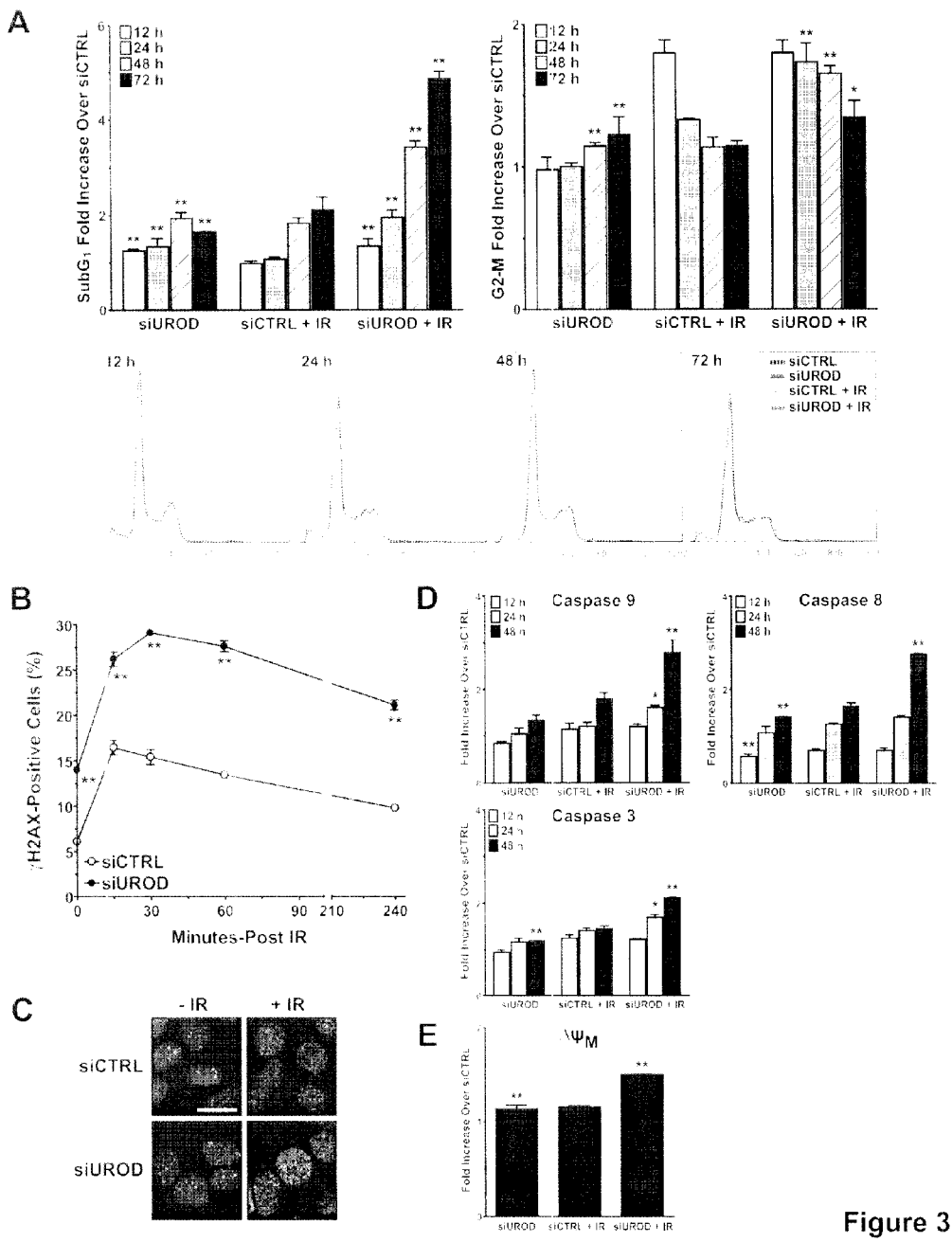
FIG. 3 shows that UROD down-regulation promotes radiation-induced cytotoxicity. (A) Flow cytometric DNA content analyses of siCTRL- or siUROD-transfected FaDu cells at 12-72 h post-IR (4 Gy). Representative histograms with gates for cell cycle distributions are shown. *$p<0.05$ and $p<0.01$, siCTRL vs. siUROD±IR at each time point. (B) Flow cytometric analyses of cellular γ-H2AX expression levels in transfected FaDu cells at 0-240 min post-IR (4 Gy). $p<0.01$, siCTRL vs. siUROD at each time point. (C) Representative images of γ-H2AX nuclear foci formation in siCTRL- and siUROD-transfected FaDu cells 30 min post-IR. Scale bar, 10 µm. (D) Flow cytometric analyses of caspase 9, 8, and 3 activation in siCTRL or siUROD-transfected FaDu cells at 12-48 h post-IR (4 Gy). *$p<0.05$ and $p<0.01$, siCTRL vs. siUROD±IR at each time point. (E) $\Delta\Psi_M$ depolarization was quantified by flow cytometry 48 h post-IR in transfected FaDu cells. $p<0.01$, siCTRL vs. siUROD±IR. Each datum represents the mean±SEM from three independent experiments.

The enhanced tumor radiosensitivity observed with UROD suppression (FIG. 1C) was mediated in part by G2-M cell cycle arrest (FIG. 3A), along with induction of double-strand DNA breaks (the most lethal type of DNA damage), reflected by increased overall γ-H2AX expression and nuclear foci formation in siUROD-plus-IR-treated FaDu cells vs. IR alone (FIG. 3B,C). The significantly prolonged G2-M arrest and concomitant increase in the $subG_1$ population suggested that the DNA damage induced by siUROD-plus-IR was more lethal than IR alone, thereby significantly augmenting apoptosis (FIG. 3A). The central role of apoptosis in siUROD-plus-IR-mediated cytotoxicity was further evident by the induction of caspase activation (FIG. 3D) and depolarization of the mitochondrial membrane potential ($\Delta\Psi_M$) (FIG. 3E), both classical hallmarks of apoptosis.

Heme biosynthesis occurs within the cytoplasm and mitochondrion (FIG. 2A); the latter being a major source of intracellular free radicals [34]. Thus, to investigate whether siUROD mediated its radiosensitizing effects via perturbation of ROS homeostasis, intracellular levels of oxidants were measured. Mitochondrial superoxide anion radicals, as well as other ROS species (hydrogen peroxide, hydroxyl radical, peroxyl radical, peroxynitrite anion), were significantly more prevalent in siUROD-plus-IR vs. IR- or siUROD-treated FaDu cells (FIG. 4A,B). Accordingly, anti-oxidants involved in maintaining cellular redox homeostasis, including superoxide dismutases (SOD1 and SOD2), glutathione peroxidase (GPX1), and mitochondrial ferritin (FTMT) were all up-regulated in FaDu cells in response to siUROD-plus-IR (FIG. 4G). This enhancement of ROS production appeared to be relatively tumor-specific (FIG. 4C,D), translating into higher survival for normal vs. FaDu cells after siUROD±IR (FIG. 4E), exposing a therapeutic window for tumor-selective radiosensitization.

Figure 5:
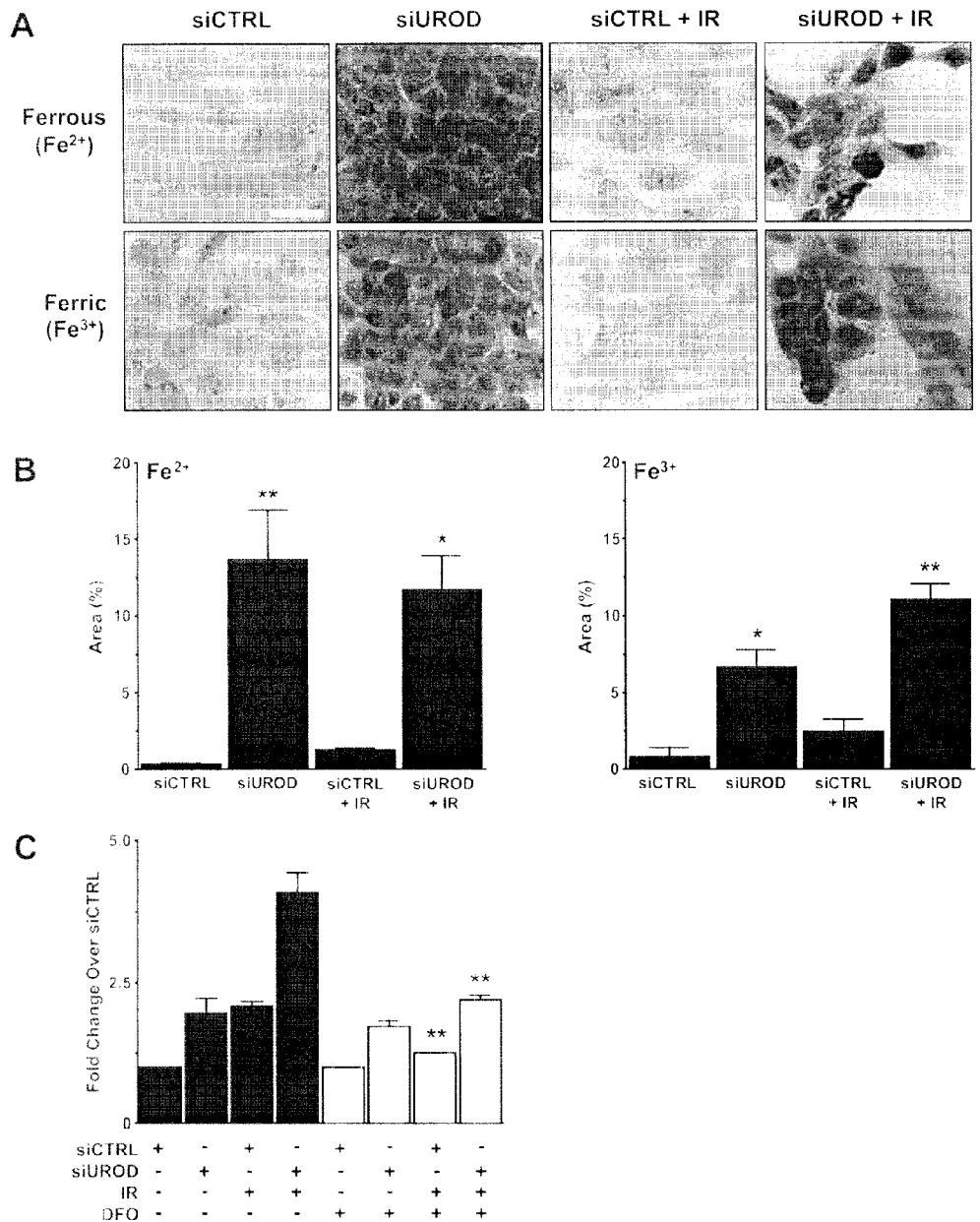
FIG. 5 shows that UROD knockdown induces intracellular iron accumulation. (A) Ferrous (Fe$^{2+}$) and ferric (Fe$^{3+}$) iron staining of siCTRL or siUROD-transfected FaDu cells at 48 h post-IR (4 Gy). Scale bar, 50 µm. (B) Quantification of intracellular Fe$^{2+}$ and Fe$^{3+}$ levels from (A). Deep-purple areas and total area of cultured cells were measured. The ratio (% area) was calculated by dividing the sum of deep-purple areas by the sum of the total area from sections. *$p<0.05$ and $p<0.01$, siCTRL vs. siUROD±IR. (C) FaDu cells transfected with siCTRL or siUROD for 24 h were treated with deferoxamine (DFO; 5 µM), and then irradiated (4 Gy) 24 h later. Apoptotic fractions were assessed by flow cytometry 72 h post-IR. $p<0.01$, −DFO vs. +DFO treatments. Each datum represents the mean±SEM from at least two independent experiments.

Mitochondria are intimately involved in iron (Fe)-trafficking for heme biosynthesis and the formation of Fe-sulfur clusters [35]. These organelles, also being the major source of ROS production, have developed efficient mechanisms to segregate free Fe from ROS, thereby preventing the production of harmful hydroxyl radicals ($^\bullet$OH) via Fenton-type reactions [36]. Accordingly, up-regulation of the Fe-sequestering FTMT anti-oxidant in siUROD±IR treated cells (FIG. 4G) was associated with markedly elevated levels of intracellular ferrous ($Fe^{2+}$) and ferric ($Fe^{3+}$) iron (FIG. 5A,B). The central role of excess cellular Fe in mediating siUROD radiosensitization was demonstrated by the significant suppression of siUROD-plus-IR-induced apoptosis in cells pre-treated with deferoxamine, a Fe-chelator, before IR (FIG. 5C). Thus, the novelty of our UROD discovery relates to the opportunity to perturb Fe homeostasis as the initiator of oxidative stress in tumor cells. When heme synthesis is disrupted via siUROD, large quantities of iron, which would normally be incorporated into PPIX to form heme, continue to be imported into the mitochondria. Upon IR, superoxide and hydroxyl radicals are formed [37], both of which can react with themselves to form $H_2O_2$, initiating the Fenton reaction and ultimately, enhancing oxidative damage and cell death.

Figure 7:
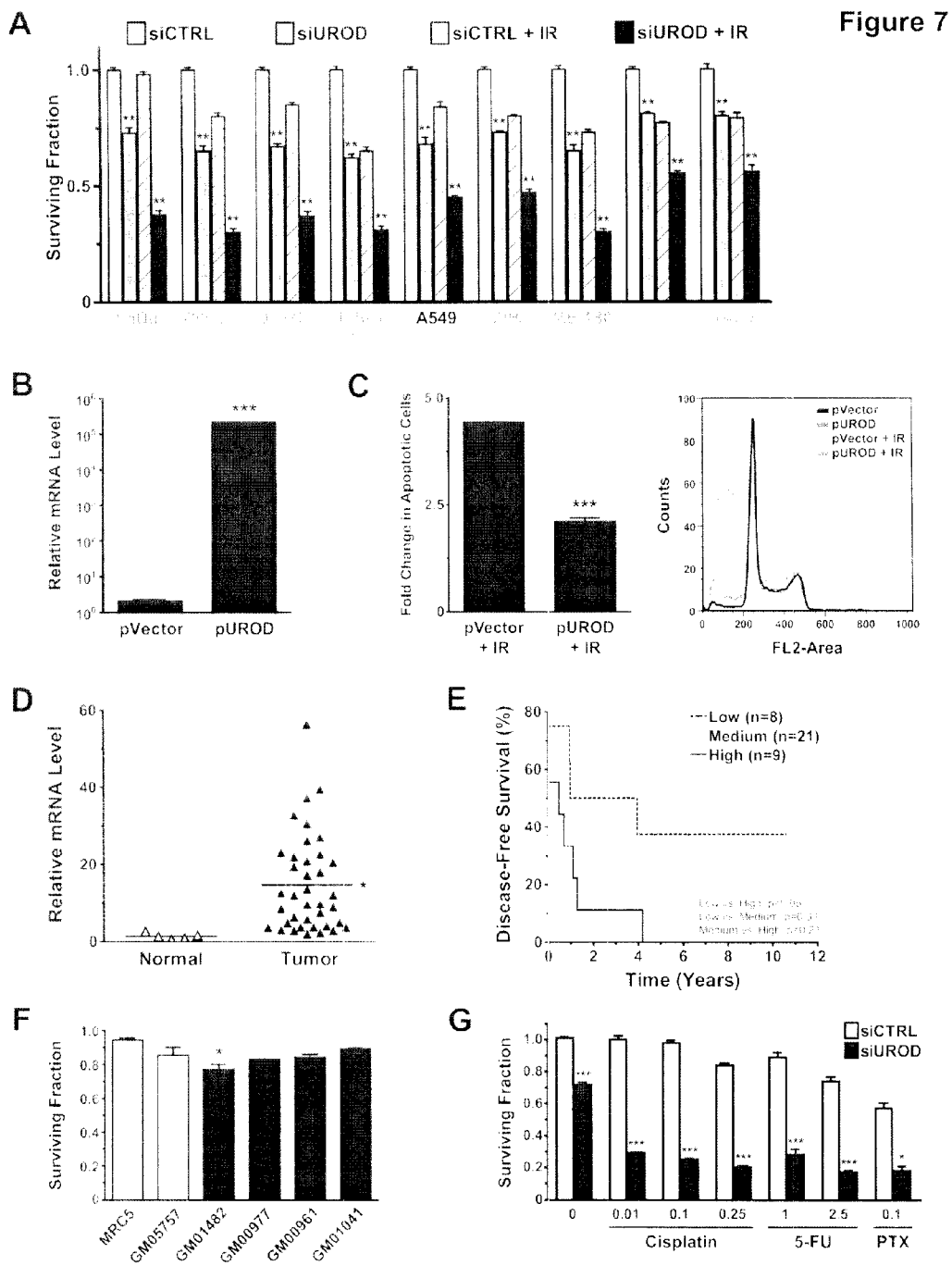
FIG. 7 shows the clinical relevance of UROD in human cancers. (A) Cell viability assessment of siCTRL or siUROD-transfected cancer cells at 96 h post-IR (2 Gy) via MTS assay. Human HNC (FaDu, C666-1, UTSCC-8, UTSCC-42a), cervix (SiHa, ME-180), breast (T47D), lung (A549), and prostate (DU-145) cancer cell lines. $p<0.01$, siCTRL vs. siUROD±IR. (B) Relative UROD mRNA expression in UTSCC-42a cells transfected with UROD-expressing plasmid (pUROD) or empty vector control (pVector) for 48 h, determined via qRT-PCR. *$p<0.001$, pVector vs. pUROD. (C) UTSCC-42a cells transfected with pUROD or pVector for 48 h were irradiated (2 Gy). Apoptotic fractions were assessed by flow cytometry 72 h post-IR. Representative histogram of cell cycle distribution is shown. ***$p<0.001$, pUROD vs. pVector+IR. (D) Total RNA was extracted from 38 HNSCC patient tumor biopsies and 5 normal laryngeal and tonsillar epithelial tissues, and assessed for relative levels of UROD mRNA expression. Fold change was determined by normalizing to β-actin levels, and comparing to the average from normal tissues. Solid line, mean fold change. *$p<0.05$, tumor vs. normal tissues. (E) Kaplan-Meier plot of disease-free survival (DFS) for the HNSCC patients from (D); trichotomized based on interquartile range (low, medium, vs. high levels of UROD mRNA expression). DFS was defined as absence of relapse or death, calculated from the time of diagnosis. Median follow-up time was 6.9 years (range 2.3-10.8 yrs). (F) Cell viability assessment of irradiated (2 Gy) primary normal human fibroblasts (MRC5, GM05757) and untransformed fibroblasts from PCT patients (GM01482, GM00977, GM00961, GM01041) 96 h post-IR via MTS assay. *$p<0.05$, MRC5 vs. PCT fibroblasts. (G) siCTRL- or siUROD-transfected FaDu cells were treated with increasing doses of Cisplatin (0.01-0.25 µM), 5-FU (1-2.5 µM), or Paclitaxel (PTX) (0.1 µM) for 24 h, then assessed for cell viability 96 h later. ***$p<0.001$ and *$p<0.05$, siCTRL±drug vs. siUROD±drug. Each datum represents the mean±SEM from three independent experiments.

There is a paucity of literature surrounding UROD and cancer. Only a few studies have reported enhanced heme biosynthesis in human cancers, wherein increased UROD activity was observed in breast tumors vs. normal tissues [38, 39]; the basis for which remained unclear. Our work represents the first such report in HNC, whereby UROD was markedly over-expressed in primary HNSCC vs. corresponding normal tissues (FIG. 7D). A potential predictive value for UROD was also revealed, wherein lower levels of pre-treatment UROD expression appeared to correlate with improved disease-free survival (DES) in HNSCC patients treated with RT (FIG. 7E); consistent with the notion that higher UROD levels conferred radioresistance, and supporting the strategy of reducing UROD to increase radiocurability. The possible role of UROD in modulating tumor radioresponse was further supported by the reversal of the radiosensitive phenotype of UTSCC-42a cells with exogenous UROD over-expression (FIG. 7B,C); thereby facilitating the selection of cancer patients who would be amenable to UROD-mediated radiosensitization.

The potential therapeutic application of siUROD in human cancers appears to be quite extensive. UROD down-regulation not only radiosensitized a wide range of solid cancers while sparing normal cells (FIGS. 7A and 4E), but also sensitized HNC cells to low doses of standard chemotherapeutic agents, such as Cisplatin, 5-fluorouracil, and Paclitaxel (FIG. 7G). Hence, siUROD could play a significant role in enhancing the outcome for both RT and chemotherapy in HNC patients, allowing lower treatment doses to be administered without compromising cure. Furthermore, a naturally occurring state of UROD deficiency is responsible for the clinical syndrome of porphyria cutanea tarda (PCT), a chronic non-fatal disorder characterized by elevated cellular porphyrin and iron levels [24]. Thus, a transient development of "PCT" during the weeks of RT and/or chemotherapy should be well-tolerated. Evidence for minimal toxicity is provided by the few case reports wherein no significant increase in toxicities was observed when PCT-cancer patients underwent RT [40-42]. In our hands, untransformed fibroblasts from familial PCT patients demonstrated minimal cytotoxicity comparable to UROD-functional primary normal human fibroblasts (FIG. 7F), corroborating our previous data that siUROD-mediated radiosensitization is tumor selective (FIG. 4E).

In conclusion, the novel identification of down-regulating UROD has significant implications in the management of human cancers for several reasons. First, its over-expression is able to prognosticate for radiation resistance, thereby potentially allowing selection of cancer patients who would be suitable for siUROD radiosensitization. Second, the therapeutic application of this approach is broad and effective in the tumor-selective enhancement of radiation and chemo-therapy efficacy. Third, there is a naturally occurring state of UROD deficiency that is non-lethal; hence, a temporary state of "PCT" would have minimal consequences to cancer patients during the few weeks of treatment. Finally, our discovery provides important insights into the translational significance of iron homeostasis and dysregulation in cancer.

Although preferred embodiments of the invention have been described herein, it will be understood by those skilled in the art that variations may be made thereto without departing from the spirit of the invention or the scope of the appended claims. All references described herein, including those listed on the following list, are incorporated by reference.

REFERENCES

1. Parkin D M, Bray F, Ferlay J, Pisani P. Global cancer statistics, 2002. CA Cancer J Clin 2005; 55: 74-108.
2. Pai S I, Westra W H. Molecular pathology of head and neck cancer: implications for diagnosis, prognosis, and treatment. Annu Rev Pathol 2009; 4: 49-70.
3. Lo K W, To K F, Huang D P. Focus on nasopharyngeal carcinoma. Cancer Cell 2004; 5: 423-428.
4. Carvalho A L, Nishimoto I N, Califano J A, Kowalski L P. Trends in incidence and prognosis for head and neck cancer in the United States: a site-specific analysis of the SEER database. Int J Cancer 2005; 114: 806-816.
5. Chin D, Boyle G M, Porceddu S, Theile D R, Parsons P G, Coman W B. Head and neck cancer: past, present and future. Expert Rev Anticancer Ther 2006; 6: 1111-1118.
6. Bourhis J, Overgaard J, Audry H, et al. Hyperfractionated or accelerated radiotherapy in head and neck cancer: a meta-analysis. Lancet 2006; 368: 843-854.
7. Pignon J P, le Maitre A, Maillard E, Bourhis J. Meta-analysis of chemotherapy in head and neck cancer (MACH-NC): an update on 93 randomised trials and 17,346 patients. Radiother Oncol 2009; 92: 4-14.
8. Bonner J A, Harari P M, Giralt J, et al. Radiotherapy plus cetuximab for locoregionally advanced head and neck cancer: 5-year survival data from a phase 3 randomised trial, and relation between cetuximab-induced rash and survival. Lancet Oncol 2010; 11: 21-28.
9. Li J H, Shi W, Chia M, et al. Efficacy of targeted FasL in nasopharyngeal carcinoma. Mol Ther 2003; 8: 964-973.
10. Yip K W, Li A, Li J H, et al. Potential utility of BimS as a novel apoptotic therapeutic molecule. Mol Ther 2004; 10: 533-544.
11. Chia M C, Shi W, Li J H, et al. A conditionally replicating adenovirus for nasopharyngeal carcinoma gene therapy. Mol Ther 2004; 9: 804-817.
12. Yip K W, Mocanu J D, Au P Y, et al. Combination bcl-2 antisense and radiation therapy for nasopharyngeal cancer. Clin Cancer Res 2005; 11: 8131-8144.
13. Yip K W, Mao X, Au P Y, et al. Benzethonium chloride: a novel anticancer agent identified by using a cell-based small-molecule screen. Clin Cancer Res 2006; 12: 5557-5569.
14. Yip K W, Ito E, Mao X, et al. Potential use of alexidine dihydrochloride as an apoptosis-promoting anticancer agent. Mol Cancer Ther 2006; 5: 2234-2240.
15. Tannock I F, Hill R P, Bristow R G, Harrington L. The Basic Science of Oncology. Fourth ed. Toronto: McGraw-Hill; 2005.
16. Cheung S T, Huang D P, Hui A B, et al. Nasopharyngeal carcinoma cell line (C666-1) consistently harbouring Epstein-Barr virus. Int J Cancer 1999; 83: 121-126.
17. Ito E, Yip K W, Katz D, et al. Potential use of cetrimonium bromide as an apoptosis-promoting anticancer agent for head and neck cancer. Mol Pharmacol 2009; 76: 969-983.
18. Cummings B, Keane T, Pintilie M, et al. Five year results of a randomized trial comparing hyperfractionated to conventional radiotherapy over four weeks in locally advanced head and neck cancer. Radiother Oncol 2007; 85: 7-16.
19. Livak K J, Schmittgen T D. Analysis of relative gene expression data using real-time quantitative PCR and the 2(-Delta Delta C(T)) Method. Methods 2001; 25: 402-408.
20. Chou T C, Talalay P. Quantitative analysis of dose-effect relationships: the combined effects of multiple drugs or enzyme inhibitors. Adv Enzyme Regul 1984; 22: 27-55.
21. Fertil B, Dertinger H, Courdi A, Malaise E P. Mean inactivation dose: a useful concept for intercomparison of human cell survival curves. Radiat Res 1984; 99: 73-84.
22. Carson F L. Histotechnology: A Self-Instructional Text. Second ed. Chicago: American Society for Clinical Pathology; 1997.
23. Gillespie D L, Whang K, Ragel B T, Flynn J R, Kelly D A, Jensen R L. Silencing of hypoxia inducible factor-1alpha by RNA interference attenuates human glioma cell growth in vivo. Clin Cancer Res 2007; 13: 2441-2448.
24. Lambrecht R W, Thapar M, Bonkovsky H L. Genetic aspects of porphyria cutanea tarda. Semin Liver Dis 2007; 27: 99-108.
25. Berg K, Selbo P K, Weyergang A, et al. Porphyrin-related photosensitizers for cancer imaging and therapeutic applications. J Microsc 2005; 218: 133-147.
26. Kennedy J C, Pottier R H, Pross D C. Photodynamic therapy with endogenous protoporphyrin IX: basic principles and present clinical experience. J Photochem Photobiol B 1990; 6: 143-148.
27. Kennedy J C, Pottier R H. Endogenous protoporphyrin IX, a clinically useful photosensitizer for photodynamic therapy. J Photochem Photobiol B 1992; 14: 275-292.
28. Moan J, Sommer S. Oxygen dependence of the photosensitizing effect of hematoporphyrin derivative in NHIK 3025 cells. Cancer Res 1985; 45: 1608-1610.
29. Mitchell J B, McPherson S, DeGraff W, Gamson J, Zabell A, Russo A. Oxygen dependence of hematoporphyrin derivative-induced photoinactivation of Chinese hamster cells. Cancer Res 1985; 45: 2008-2011.
30. Kulka U, Schaffer M, Siefert A, et al. Photofrin as a radiosensitizer in an in vitro cell survival assay. Biochem Biophys Res Commun 2003; 311: 98-103.
31. Evensen J F. The use of porphyrins and non-ionizing radiation for treatment of cancer. Acta Oncol 1995; 34: 1103-1110.
32. Schaffer M, Schaffer P M, Corti L, et al. Photofrin as a specific radiosensitizing agent for tumors: studies in comparison to other porphyrins, in an experimental in vivo model. J Photochem Photobiol B 2002; 66: 157-164.
33. Schaffer M, Ertl-Wagner B, Schaffer P M, et al. Porphyrins as radiosensitizing agents for solid neoplasms. Curr Pharm Des 2003; 9: 2024-2035.
34. Valko M, Leibfritz D, Moncol J, Cronin M T, Mazur M, Telser J. Free radicals and antioxidants in normal physiological functions and human disease. Int J Biochem Cell Biol 2007; 39: 44-84.
35. Hower V, Mendes P, Torti F M, et al. A general map of iron metabolism and tissue-specific subnetworks. Mol Biosyst 2009; 5: 422-443.
36. Fenton H J H. Oxidation of tartaric acid in presence of iron. J Chem Soc 1894; 65: 899-910.
37. Tannock I F, Hill S A, Bristow R G, Harrington L. The Basic Science of Oncology. Fourth ed. Toronto: McGraw-Hill; 2005.
38. Navone N M, Polo C F, Frisardi A L, Andrade N E, Battle A M. Heme biosynthesis in human breast cancer—mimetic "in vitro" studies and some heme enzymic activity levels. Int J Biochem 1990; 22: 1407-1411.

39. Navone N M, Frisardi A L, Resnik E R, Baffle A M, Polo C F. Porphyrin biosynthesis in human breast cancer. Preliminary mimetic in vitro studies. Med Sci Res 1988; 16: 61-62.
40. Maughan W Z, Muller S A, Perry H O. Porphyria cutanea tarda associated with lymphoma. Acta Derm Venereol 1979; 59: 55-58.
41. Schaffer M, Schaffer P M, Panzer M, Wilkowski R, Duhmke E. Porphyrias associated with malignant tumors: results of treatment with ionizing irradiation. Onkologie 2001; 24: 170-172.
42. Gunn G B, Anderson K E, Patel A J, et al. Severe radiation therapy-related soft tissue toxicity in a patient with porphyria cutanea tarda: A literature review. Head Neck 2009.

The invention claimed is:

1. A method for sensitizing a subject with cancer to a cancer therapy comprising administering to the subject a sensitizing amount of an agent comprising an siRNA that downregulates or inhibits uroporphyrinogen decarboxylase (UROD), wherein
the cancer is head and neck cancer and
the cancer therapy is at least one of cisplatin, 5-FU, paclitaxel, and radiation.

2. The method of claim 1, wherein the head and neck cancer is selected from the group consisting of cancers of the lip, nasal cavity, oral cavity, sinuses, pharynx and larynx.

3. The method of claim 1, wherein the cancer therapy is radiation therapy.

4. The method of claim 1, wherein the cancer therapy is Cisplatin, 5-FU or Paclitaxel.

5. The method of claim 3, wherein the radiation therapy is therapy using ionizing radiation.

6. The method of claim 3, wherein the radiation therapy is therapy using non-ionizing radiation.

7. The method of claim 6, wherein the radiation therapy is photodynamic therapy.

8. The method of claim 1, wherein the siRNA is SEQ ID NOs. 2 and 3, or 5 and 6.

9. The method of claim 2, wherein the cancer is selected from nasopharyngeal carcinoma and laryngeal carcinoma.

* * * * *